United States Patent
Sosiak et al.

(10) Patent No.: US 6,537,273 B1
(45) Date of Patent: Mar. 25, 2003

(54) DEVICE AND METHOD FOR REMOVING LARGE TISSUE MASSES

(76) Inventors: Alexander K. D. Sosiak, 69-57 Alderton St., #1, Rego Park, NY (US) 11374; Borys R. Krynyckyi, 1550 Laurel Ct., Manasquan, NJ (US) 08736

( * ) Notice: Subject to any disclaimer, the term of this patent is extended or adjusted under 35 U.S.C. 154(b) by 118 days.

(21) Appl. No.: 09/609,452

(22) Filed: Jun. 30, 2000

Related U.S. Application Data

(60) Provisional application No. 60/165,015, filed on Nov. 12, 1999, provisional application No. 60/142,280, filed on Jul. 2, 1999, provisional application No. 60/142,279, filed on Jul. 2, 1999, provisional application No. 60/142,292, filed on Jul. 2, 1999, provisional application No. 60/142,291, filed on Jul. 2, 1999, and provisional application No. 60/165,014, filed on Nov. 12, 1999.

(51) Int. Cl.$^7$ .............................................. A61B 18/18
(52) U.S. Cl. ............................ 606/41; 606/45; 606/47; 606/48; 606/170
(58) Field of Search .................... 606/113, 114, 606/41, 45, 46, 47, 50

(56) References Cited

U.S. PATENT DOCUMENTS

| | | |
|---|---|---|
| 1,609,014 A | 11/1926 | Dowd |
| 1,615,494 A | 1/1927 | Waring |
| 1,931,740 A | 10/1933 | Ryan |
| 2,043,782 A | 6/1936 | Sprosty |
| 3,244,169 A | 4/1966 | Baxter |
| 3,472,230 A | 10/1969 | Fogarty |
| 3,828,790 A | 8/1974 | Curtiss et al. |
| 3,955,578 A | 5/1976 | Chamness et al. |
| 4,311,143 A | 1/1982 | Komiya |
| 4,326,530 A | 4/1982 | Fleury, Jr. |
| 4,345,599 A | 8/1982 | McCarrell |
| 4,493,320 A | 1/1985 | Treat |
| 4,503,855 A | 3/1985 | Maslanka |
| 4,590,938 A | 5/1986 | Segura et al. |
| 4,619,260 A | 10/1986 | Magill et al. |
| 4,718,419 A | 1/1988 | Okada |
| 4,905,691 A | 3/1990 | Rydell |
| 5,026,371 A | 6/1991 | Rydell et al. |
| 5,033,362 A | 7/1991 | Huckestein |
| 5,066,293 A | 11/1991 | Furumoto |
| 5,078,716 A | 1/1992 | Doll |
| 5,123,906 A | 6/1992 | Kelman |
| 5,158,561 A | 10/1992 | Rydell et al. |
| 5,171,233 A | 12/1992 | Amplatz et al. |
| 5,171,314 A | 12/1992 | Dulebohn |
| 5,190,542 A | 3/1993 | Nakao et al. |
| 5,201,740 A | 4/1993 | Nakao et al. |
| 5,201,741 A | 4/1993 | Dulebohn |
| 5,226,429 A | 7/1993 | Kuzmak |
| 5,318,564 A | 6/1994 | Eggers |
| 5,320,627 A | 6/1994 | Sorensen et al. |
| 5,330,482 A | 7/1994 | Gibbs et al. |
| 5,336,277 A | 8/1994 | Nakao et al. |
| 5,342,371 A | 8/1994 | Welter et al. |
| 5,387,219 A | 2/1995 | Rappe |

(List continued on next page.)

FOREIGN PATENT DOCUMENTS

DE      4212430 A1      10/1993

OTHER PUBLICATIONS

Endosc. Surg. Allied Tech. Journal, "Ultrasonic Dissection In Combination With High Frequency Surgery", 1994.

*Primary Examiner*—Linda C. M. Dvorak
*Assistant Examiner*—David M. Ruddy
(74) *Attorney, Agent, or Firm*—Morgan & Finnegan, L.L.P.

(57) ABSTRACT

The invention provides a device and method for reducing or segmenting a large tissue mass in a body cavity during a minimally invasive surgery. This is accomplished with using a device that uses both mechanical and electro-surgical mechanisms by creating an electrical path between two electrodes through the tissue mass. The invention uses an isolation bag to insulate the electrical path created from the body cavity.

46 Claims, 29 Drawing Sheets

U.S. PATENT DOCUMENTS

| | | | |
|---|---|---|---|
| 5,397,320 A | * 3/1995 | Essig et al. | 606/45 |
| 5,403,276 A | 4/1995 | Schechter et al. | |
| 5,417,697 A | 5/1995 | Wilk et al. | 606/113 |
| 5,443,472 A | * 8/1995 | Li | 606/114 |
| D362,504 S | 9/1995 | Younker et al. | |
| 5,462,553 A | 10/1995 | Dolgin | |
| 5,522,819 A | 6/1996 | Graves et al. | |
| 5,569,269 A | 10/1996 | Hart et al. | |
| 5,611,803 A | 3/1997 | Heaven et al. | |
| 5,643,281 A | 7/1997 | Suhocki et al. | |
| 5,643,288 A | 7/1997 | Thompson | |
| 5,643,304 A | 7/1997 | Schechter et al. | |
| 5,669,876 A | 9/1997 | Schechter et al. | |
| 5,685,840 A | 11/1997 | Schechter et al. | |
| 5,735,289 A | * 4/1998 | Pfeffer et al. | 606/113 |
| 5,746,747 A | 5/1998 | McKeating | |
| 5,759,187 A | 6/1998 | Nakao et al. | 606/114 |
| 5,782,840 A | 7/1998 | Nakao | |
| 5,788,709 A | 8/1998 | Riek et al. | |
| 5,807,267 A | 9/1998 | Bryars et al. | |
| 5,810,764 A | 9/1998 | Eggers et al. | |
| 5,814,044 A | 9/1998 | Hooven | 606/48 |
| 5,814,052 A | 9/1998 | Nakao et al. | |
| 5,843,019 A | 12/1998 | Eggers et al. | |
| 5,873,876 A | 2/1999 | Christy | |
| 5,895,392 A | 4/1999 | Riek et al. | |
| 5,906,620 A | 5/1999 | Nakao et al. | |
| 5,906,621 A | 5/1999 | Secrest et al. | |
| 5,968,056 A | 10/1999 | Chu et al. | |
| 5,989,264 A | 11/1999 | Wright | |
| 5,997,547 A | 12/1999 | Nakao et al. | |
| 6,004,330 A | 12/1999 | Middleman et al. | |
| 6,015,415 A | 1/2000 | Avellanet | |
| 6,117,133 A | * 9/2000 | Zappala | 606/46 |
| 6,152,932 A | * 11/2000 | Ternstrom | 606/114 |

* cited by examiner

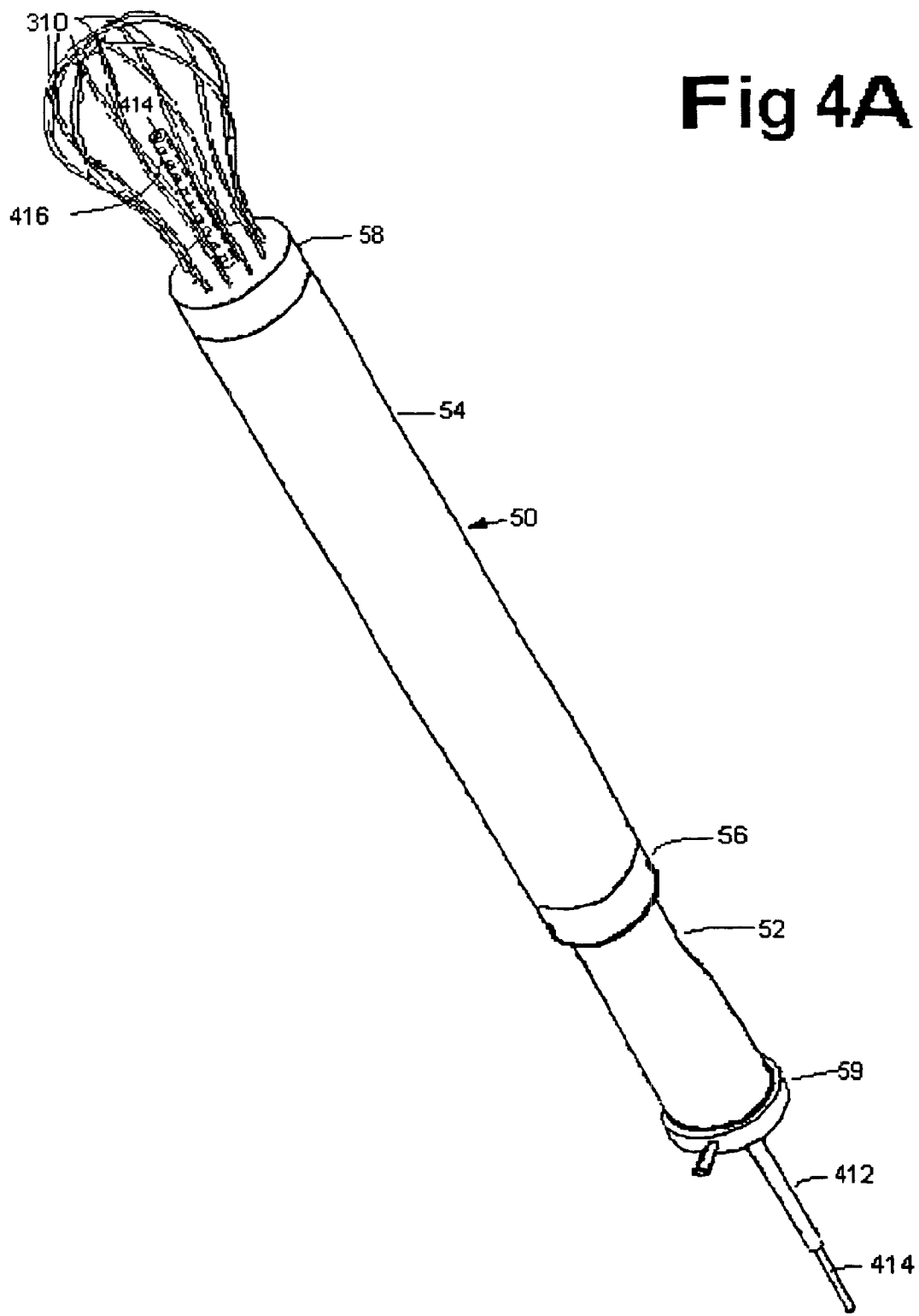

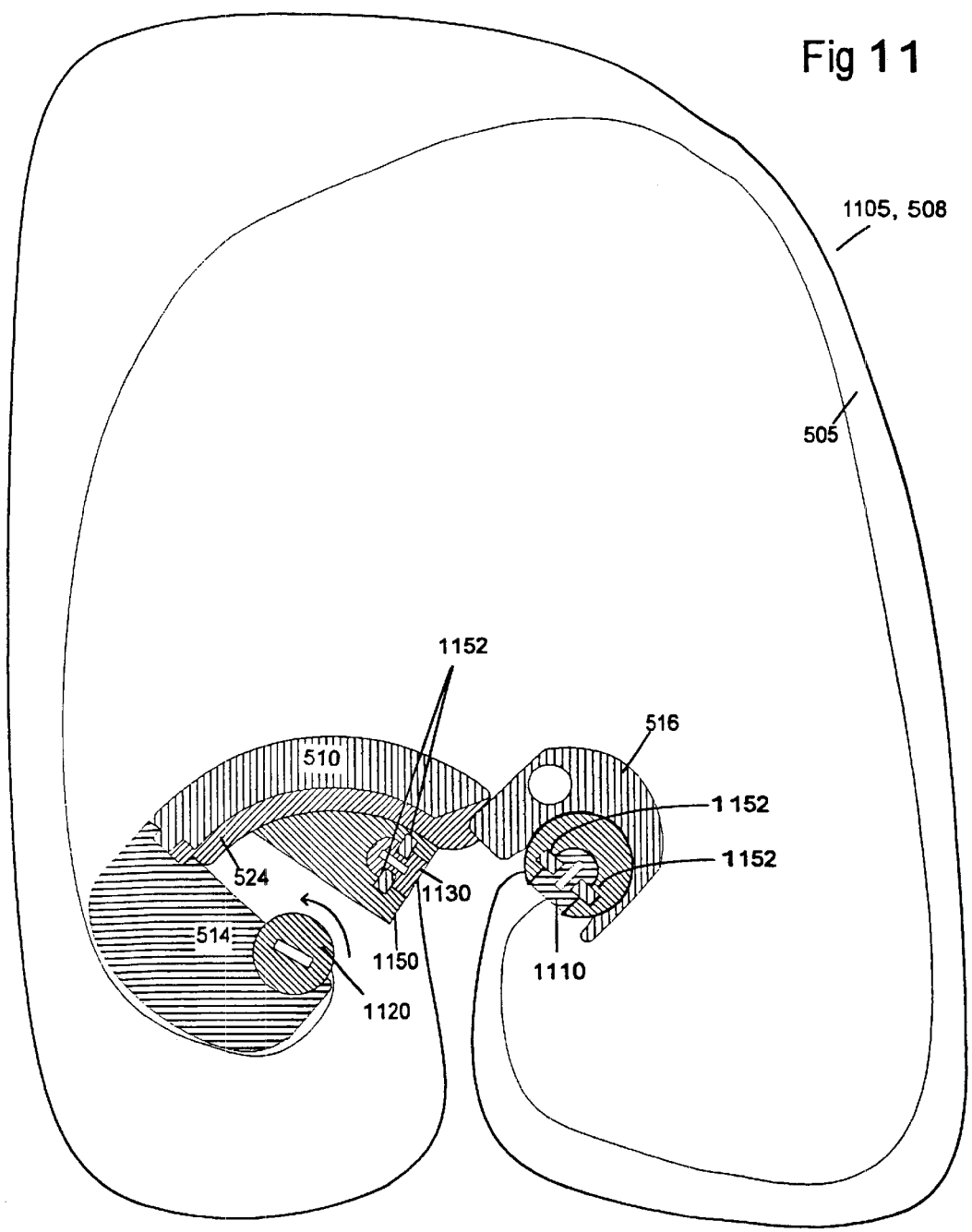

DEVICE AND METHOD FOR REMOVING LARGE TISSUE MASSES

This application claims the benefit of Provisional application Ser. No. 60/165,015 filed Nov. 12, 1999; which claims benefit of No. 60/142,280, filed Jul. 2, 1999, which claims benefit of No. 60/142,279, filed Jul. 2, 1999, which claims benefit of No. 60/142,292, filed Jul. 2, 1999, which claims benefit of No. 60/142,291, filed Jul. 2, 1999, which claims benefit of No. 60/165,014, filed Nov. 12, 1999.

BACKGROUND OF THE INVENTION

1. The Field of the Invention

The present invention relates generally to a medical device, and, more particularly, to a surgical instrument assembly for reducing and removing tissue masses from a body during minimally invasive procedures, such as laparoscopic surgery.

2. Description of the Related Art

In the past, the standard procedure for removing a large tumor, diseased organ or tissue mass from a patient was accomplished by open surgery. As a result of the open surgery, patients commonly suffered postoperative pain, long hospital stays, long recovery periods, and large scars where the incisions were made.

With the advent of minimally invasive surgery, such as, for example, laparoscopic surgery, large tissue masses may be removed by making smaller incisions, decreasing postoperative pain and hospitalization time and providing a faster return to functional status for the patient as compared to open surgery.

In recent years, there has been an unprecedented increase in the number of patients undergoing treatment with interbody devices for segmenting or snagging the large tumor, diseased organ or tissue mass to be removed. The use of various devices during laparoscopic surgery has amplified the surgeon's precision and quality and has shortened the length of operative procedures.

One method of reducing the size of large tissue masses in a body cavity is to use a device such as a morcellator. A morcellator is used in conjunction with a tissue isolation bag to mechanically reduce the size of the object by grinding, coring or shaving the object. However, morcellators are generally very slow, which increases the risk and cost associated with the operating procedure, and frequently do not remove tissue in identifiable form to allow later pathology.

Other methods of reducing the size of large tissue masses include use of a surgical snare or wire cage to retrieve, segment or cut the tissue mass by the combination of mechanical forces and heat. However, the tissue mass frequently escapes from the capturing instrumentality or is damaged beyond identifiable form. In addition, the tissue mass frequently jams against the end of the trochar inserted into the bag for delivering the device, disrupting the procedure.

3. Summary of the Invention

The invention provides a device and a method that overcome these problems and results in a higher quality of minimally invasive surgery. In addition to providing better quality reduction or segmentation control, the invention offers a quicker and more economical procedure as compared to known minimally invasive procedures and devices.

According to one embodiment, a device for reducing tissue mass comprises an isolation bag surrounding the tissue mass. The bag has an inner conductive layer which constitutes a first electrode. The device also comprises a trochar extending into the isolation bag and a probe introduced into the bag through the trochar to contact the tissue mass. The probe constitutes a second electrode. A power source supplies electrical current to the probe and the inner layer of the bag. A current bridge is created through the tissue mass between the probe and the inner layer of the bag so that the probe effectively ablates or vaporizes the tissue mass.

According to another embodiment, a device for segmenting tissue mass comprises an isolation bag having an open end. The bag is capable of being introduced into a body cavity while in a collapsed state and of being expandable from the collapsed state to an expanded state to surround the tissue mass when inserted into the body cavity. The inside of the bag containing the tissue mass thermally and electrically insulated from the body cavity. The device also comprises a trochar having a distal cap end and a moveable proximal cap end and a cage of electrosurgical wires capable of surrounding the tissue mass. The wires have ends connected to the proximal cap end. The cage of electrosurgical wires are held in formation by the distal cap end of the trochar and retracted by moving the proximal cap end. The device also comprises a center rod passing through the trochar and into the bag and a source of electrical current for supplying current to the cage of electrosurgical wires and the center rod. The combination of the center rod and the cage of electrosurgical wires work to reduce and segment the tissue mass by both mechanical and electrosurgical means.

According to another embodiment of the invention, a device for reducing tissue mass in a body cavity comprises an insulated bag having an open end. The bag is capable of being introduced into the body cavity while in a collapsed state and being expandable from the collapsed state to an expanded state to surround the tissue mass. The open end of the bag containing the tissue mass is withdrawn from the body cavity. The device also comprises a trochar having a distal end and a wall comprising a right end cap, a left end cap, and a conductive surface on one side of the wall facing the tissue mass. The wall is deployable into the bag through the trochar. At least one wire loop is positioned within the bag. The loop has ends that pass through the right and left end caps of the wall. The device further comprises tensioning means for applying tension to at least one of the ends of the loop to reduce the diameter of the loop so that the tissue mass contacts the conductive surface of the wall. The device also comprises a source of electrical current for supplying current to the conductive surface and the wire loop. An electrical path is formed between the loop and the conductive surface. The combination of the loops and the conductive surface work to reduce or segment the tissue mass.

In another aspect, the invention is directed to a method for segmenting a tissue mass in a body cavity comprising steps of surrounding the tissue mass with an isolation bag, the isolation bag including an open end; withdrawing the open end of the isolation bag to the outside of the body cavity; and segmenting the tissue mass into a plurality of smaller pieces by creating an electrical path between at least one wire loop and a deployable electrically conducting surface by applying tension to the wire loops. In another aspect, the method comprises the step of segmenting the tissue mass into a plurality of smaller pieces by creating an electrical path between an electrically conducting inner layer of the isolation bag and a probe having at least one electrically exposed electrode.

BRIEF DESCRIPTION OF THE DRAWINGS

FIG. 4A is an perspective view of a fourth embodiment of the invention illustrating a cage of wires and a center rod;

FIG. 11 is a top view of another embodiment of the invention illustrating an alternative docking system for the wire grid assembly, support sheet or isolation bag;

DETAILED DESCRIPTION OF THE PREFERRED EMBODIMENTS

Figure 1:
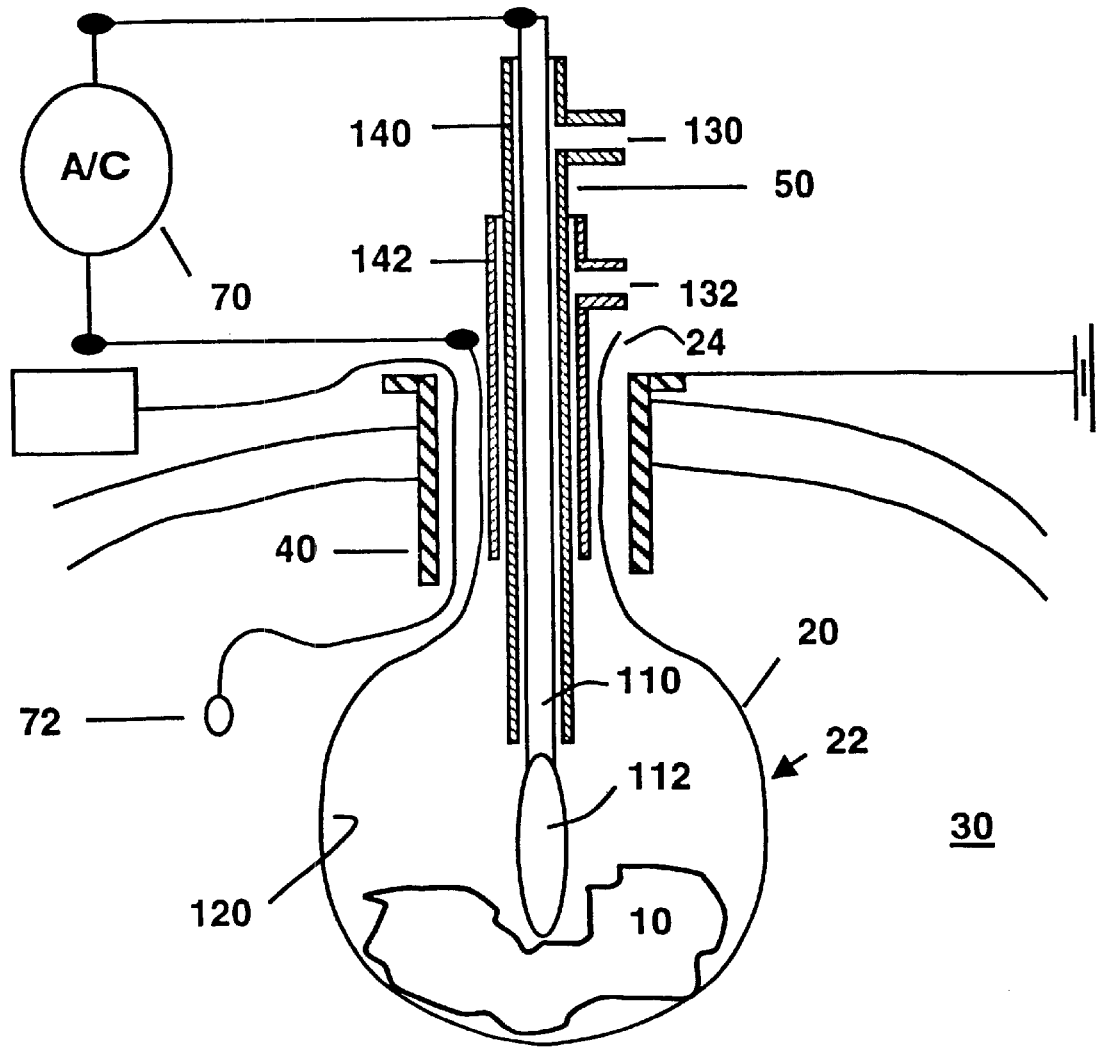
FIG. 1 is a side view of a first embodiment of the invention illustrating a probe comprising a center electrode.

The present invention is a surgical instrument assembly for reducing tissue mass in a body cavity during minimally invasive medical procedures, such as, for example, laparoscopic surgery. The device uses the tissue mass as a current path between two electrodes that serve as poles of an A/C generator. As will be discussed in more detail below, current is caused to flow between the poles to aid in cutting or vaporizing the tissue mass. The current may be supplied from individual control units and generators connected to each component. Alternatively, the device may incorporate a multi-channel control unit to control the supply of current to the various components.

The device is constructed primarily of electrically conductive and non-conductive or insulated components and may use both mechanical and electro-surgical means to reduce the tissue mass. The electrically conductive components of this invention may be made of, for example, stainless steel, copper, silver, carbon film, or any other metal or metal alloy, or the like. The electrically conductive material must not break or fracture under high temperature and high current conditions and must not rust easily. The electrically non-conductive or insulated components may be made of, for example, Teflon®, rubber, glass, ceramics, vinyl, polypropylene, polyethylene or other plastics, or the like. The insulated materials may also be reinforced with, for example, glass, fiberglass, composites, or the like.

The invention incorporates an isolation or containment bag 20. The bag includes an electrically non-conductive or insulated outer layer or surface 22 that is physically strong and resistant to tear. This outer layer protects the patient from electrical or thermal damage by containing the electrically exposed components or circuit within the bag and out of direct contact with the walls of body cavity 30. This device assures that the entire process of cutting or vaporizing the tissue mass takes place inside the isolation bag.

The bag is flexible so that it may be folded and inserted into the body cavity. During an operation, and after an incision is made, the bag is introduced into the body cavity through a small incision and manipulated to surround the tissue mass by known surgical methods. It is understood that the tissue mass has already been surgically detached within the body cavity. The invention may incorporate an outer trochar cannula, shealth or tube 40 to facilitate insertion of the bag into the body cavity.

Once the bag has been manipulated to surround the tissue mass, open end 24 of the bag is pulled out of the incision (through the outer trochar) to prevent escape of diseased tissue into the surrounding areas and to protect the entire body cavity from electrical or thermal damage. In one embodiment, the outer layer of the isolation bag includes sensors to detect current leakage that might occur if the bag rips or tears, or to monitor temperature. In another embodiment, a separate detector 72 may be incorporated to detect current leakage or to monitor temperature in the body cavity.

The invention may incorporate an inner, delivery trochar cannula, sheath or tube 50 to facilitate the insertion of the components of the invention into the body cavity of the patient. This second trochar extends into the bag containing the tissue mass. As will be discussed in more detail below, this trochar may also serve as a conduit for electrical wires, coolant and serve as an irrigation conduit.

Certain preferred embodiments of the present invention will now be described in detail with reference to the drawings. Turning first to FIG. 1, a surgical instrument assembly for reducing tissue masses within a body according to one embodiment of the present invention is shown. In this embodiment, the tissue mass 10 is reduced or destroyed by a current supplied to a probe 110 and an inner layer 120 of the isolation or containment bag 20. The current supplied to probe 110 cuts and coagulates tissue mass 10 upon contact.

The isolation or containment bag of this embodiment may include an electrically conductive inner layer or surface 120 incorporated as part of bag 20. Alternatively, this inner layer 120 is made of a separate metal or carbon film, grid, net or mesh layer of electrically conductive material which is attached to the inner portion of the bag. The inner layer 120 of bag 20 constitutes a first. electrode that serves as one pole of an A/C circuit.

In the embodiment shown in FIG. 1, probe 110 includes an exposed conductive electrode 112 at its distal end. This electrode 112 serves as another pole of the A/C circuit. The exposed electrode 112 can be shaped in a variety of forms and sizes.

As mentioned above, tissue mass 10 serves as a current path or circuit between the first pole—inner bag layer 120—and the second pole—probe 110 (comprising electrode 112). The inner layer 120 of the bag and probe 110 are coupled to terminals of a power supply generator 70. Current supplied to probe 110 and to inner layer 120 of the bag form a closed circuit within the bag, protected from body cavity 30. A large amount of current can be used since the circuit is isolated from the rest of the body and can be cooled by channels incorporated in probe 110. This would greatly reduce the time required to reduce the diseased tissue mass.

Figure 2:
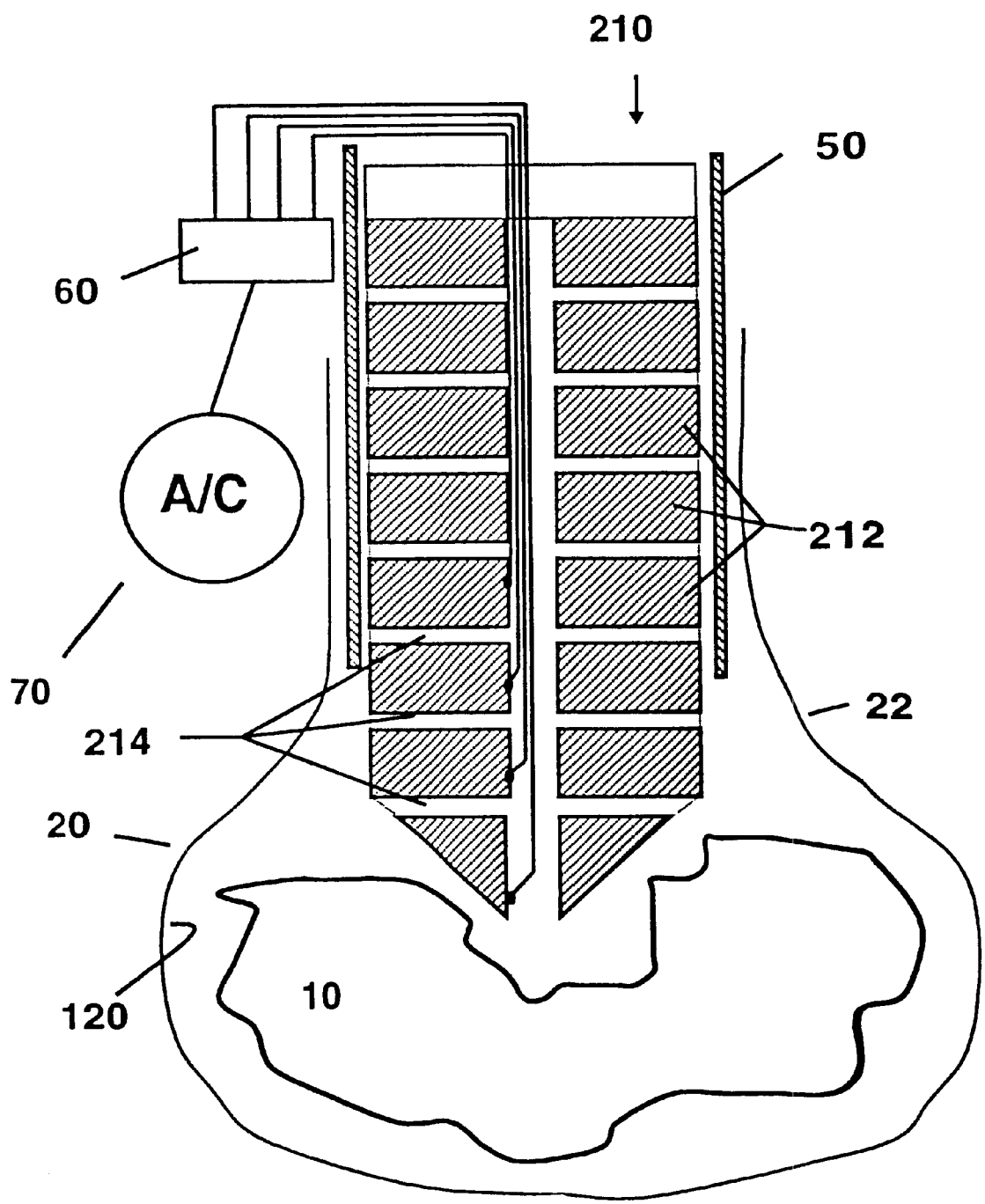
FIG. 2 is a schematic of a second embodiment of the invention illustrating a probe comprising a plurality of independent electrodes each coupled to a multi-channel control unit.

In an alternate embodiment, as shown in FIG. 2, the probe 210 is constructed of a plurality of individual, independent electrically conductive electrodes 212 separated by insulating members 214. The independent conductive electrodes 212 and insulating members 214 may be shaped, for example, as quarter circle disks that form, when stacked together, a rod-like arrangement.

Each of the independent conductive electrodes 212 may be coupled to a multi-channel control unit 60 by electrical conduit means 62 such as, for example, high conductive wire. Current is supplied to the control unit 60 from a main generator current source 70. The control unit 60 acts similar to a current switch. The multi-channel control unit 60 is programmed to determine whether any of the independent conductive electrodes 212 have shorted out by contacting inner layer 120 of isolation bag 20. If any of the independent conductive electrodes 212 contact inner layer 120 of bag 20, control unit 60 shuts down that particular independent electrode 212 by ceasing or cutting off the current flow to that electrode. The other independent conductive electrodes 212 would continue to receive current and function until control unit 60 determines a short circuit has occurred with any of those electrodes.

In alternate embodiments, each independent electrode is associated with its own control unit and generator. In yet another embodiment, two or more electrodes are connected to a common control unit and generator.

The pressure inside the bag 20 can be controlled by varying the pressure of a gas or liquid at two ports 130, 132 and distal and proximal transport channels 140, 142. By adjusting the pressure inside, the bag 20 may be controlled to collapse around tissue mass 10 (by applying negative pressure), bringing the tissue mass closer to probe 110 to facilitate the destruction or vaporization. Alternatively, coolant may be circulated through ports 130, 132 and distal and proximal transport channels 140, 142 to cool the system to prevent thermal injury to the patient. The coolant may be a variety of materials, including, for example, non-conductive compounds.

Probe 120, 220 is used to cut and ablate the tissue mass 10 using alternating current. After the tissue mass has been effectively vaporized or reduced into smaller pieces, probe 120, 220 and delivery trochar 50 are removed from bag 20. The thin pieces of tissue are then removed from the bag using instruments (e.g. forceps) commonly used during surgery. If the tissue pieces are small enough and pliable enough, the entire bag 20 could be removed in one operation without having to first remove the individual tissue pieces.

Figure 3A:
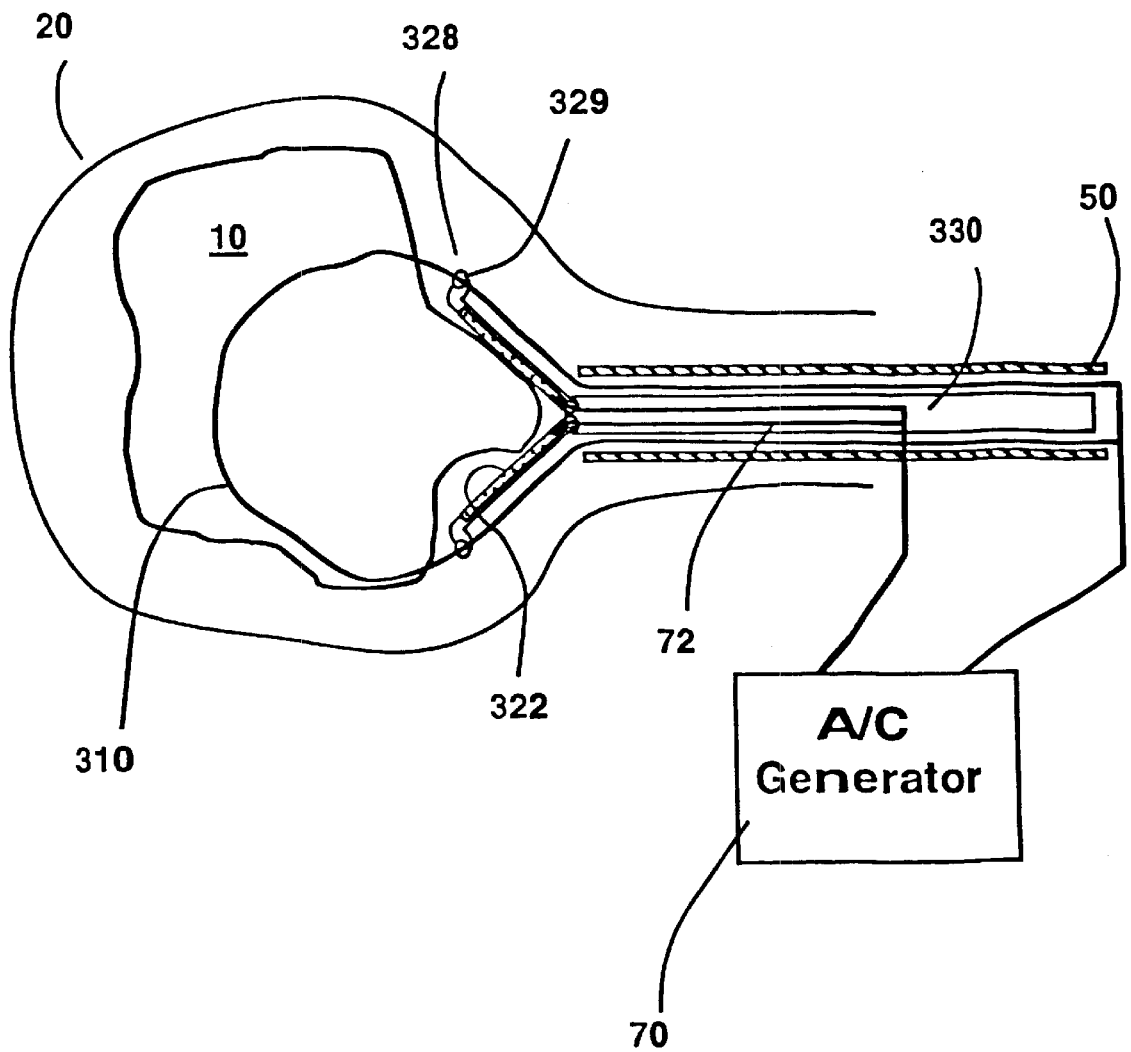
FIG. 3A is a side view of a third embodiment of the invention using deployable swing arms and wire grid assembly to reduce the tissue mass.

In another example of the invention, FIG. 3A illustrates a device using both mechanical and electro-surgical mechanisms to reduce tissue mass 10 into smaller pieces within isolation bag 20. As shown, tissue mass 10 is between at least one wire or ribbon loop 310 and a plurality of swing arms 320. Both wire loop(s) 310 and swing arms 320 are deployable into the isolation bag 20 through delivery trochar 50.

As shown in FIG. 3A, a support shaft 330 is slidably received by delivery trochar 50. The swing arms 320 are pivotably connected to support shaft 330. The support shaft 330 supports the swing arms 320 and serves as a conduit for wires 72 connected to swing arms 320 from current supply generator 70. The support shaft 330 may also include channels for temperature sensors, video, and irrigation.

Each swing arm 320 includes an outer conductive surface 322 facing tissue mass 10 while fully extended in isolation bag 20. The outer surfaces 322 are coupled to the A/C generator 70 by wires 72. As will be described in more detail below, the outer conductive surfaces 322 of swing arms 320 constitute a first electrode that serves as one pole of A/C generator 70.

Figure 3B:
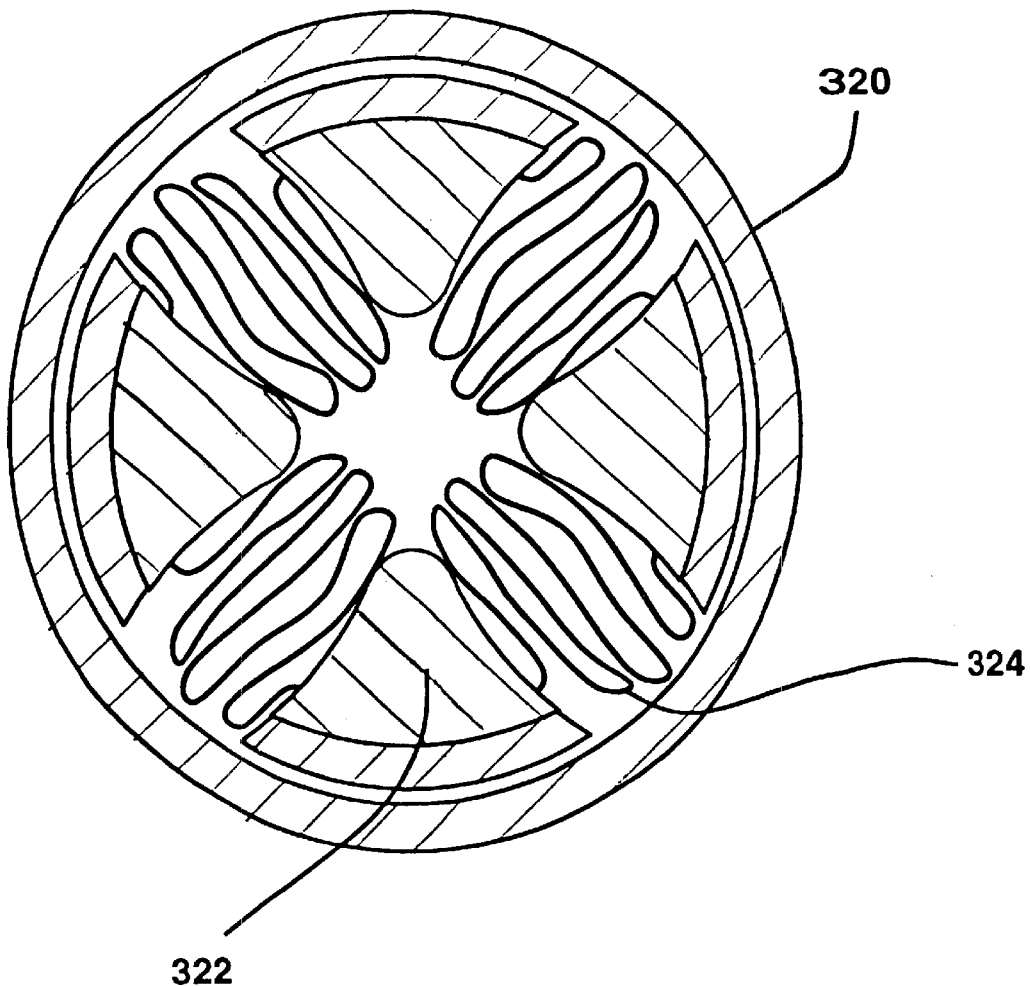
FIG. 3B is an end view of the swing arms having membranes that increase the surface area of contact of the tissue mass.

In one embodiment, adjacent outer surfaces 322 of swing arms 320 are connected by a conducting membrane 324 made of, for example, pliable woven or non-woven metal sheets, conducting cloth mylar, or the like. The conducting membranes 324 increase the effective surface area (FIG. 3B) of the pole created by the outer surfaces 322 of the swing arms 320 by bridging or connecting the individual outer surfaces 322. The benefit of a larger surface area increases the contact and interaction with the tissue mass 10 and provides added strength to swing arms 320 during the tissue cutting process, as will be described in more detail below. The swing arms 320, with attached conducting membranes 324, can be deployed from delivery trochar 50 in a reverse umbrella-like fashion. Without the swing arms and membrane (particularly the surface facing and supporting the tissue mass), the tissue mass tends to jam against or disrupt the delivery trochar as the wires are retracted to reduce the tissue mass. With the swing arms and membrane, the tissue mass is provided with a "cutting board" surface, preventing the tissue mass from disrupting the delivery trochar and the operation.

Preferably, support shaft 330, inner portions 326 and ends 328 of swing arms 320 are made of a non-conductive or insulated material. Inner portion 326 of swing arms 320 are also preferably made of a load bearing material to support outer conductive surface 322.

Wire or ribbon loops 310 are made of a highly conductive material such as, for example, spring steel. As shown in FIG. 3A, the wire loops 310 are deployed into isolation bag 20 by feeding the wire loop through delivery trochar 50. The ends 328 of the swing arms may include wire guides 329. These wire guides 329 are made of, or lined with, a non-conductive or insulated material so that the wires 310 do not contact or short out on the outer surfaces 322 of swing arms 320. Wire loops 310 may be coupled directly to the A/C generator. The wire loops constitute a second electrode that serves as one pole of A/C generator 70.

Figure 3C:
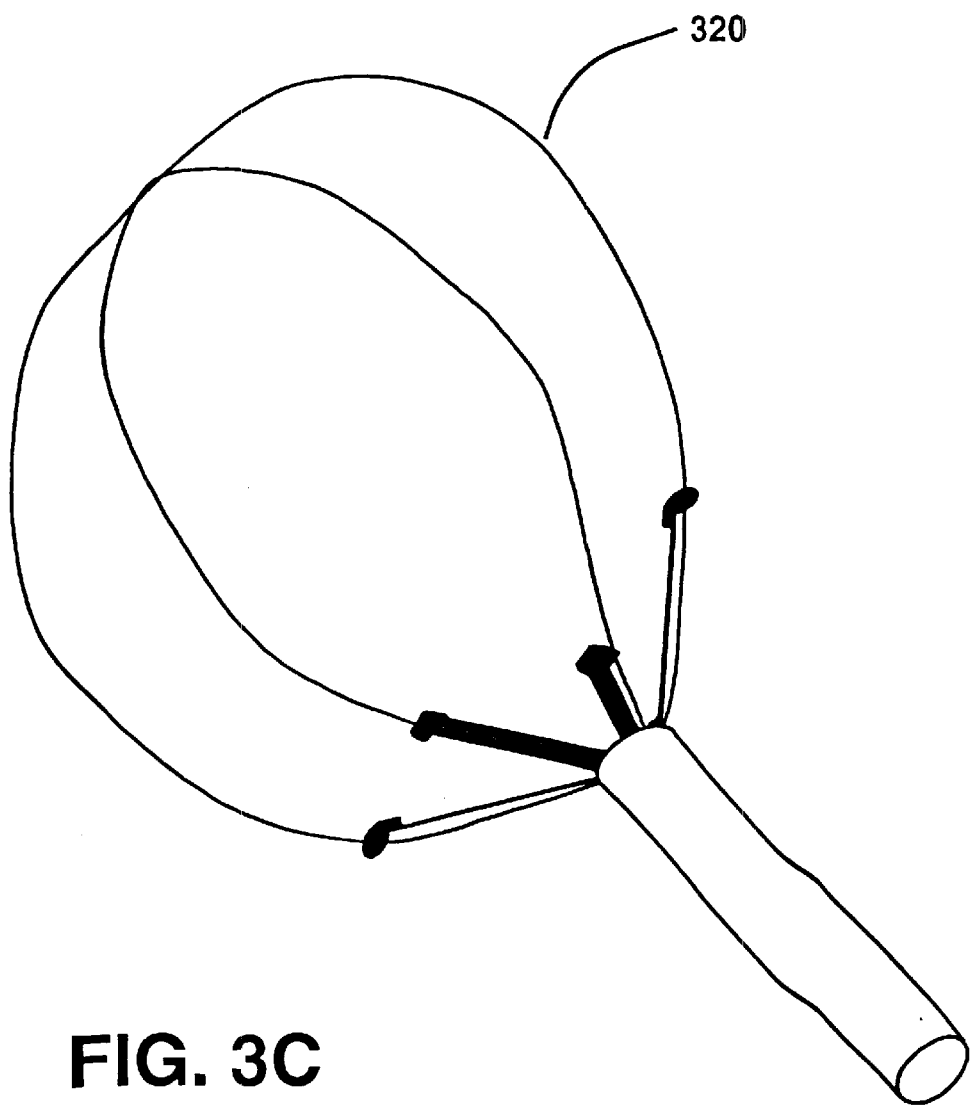
FIG. 3C is an perspective view of the "egg-beater" configuration of the wire grid assembly.

When fully deployed, the wire loops assume a basket-type configuration due to the physical characteristics programmed or preformed into the wire loops during the annealing process during the production of the wires. In one embodiment in which at least two wire loops are used, the wire loops are arranged in an "egg beater-like" configuration (FIG. 3C). When fully deployed, this "egg beater-like" configuration permits the tissue mass 10 to be inserted within the space defined or created by the wire loops.

The loops may be made of a shape memory alloy which is highly elastic or which has been treated to return to a particular configuration when deployed from the delivery trochar. Shape memory alloys exhibit the useful characteristic of being capable of changing physical shape upon heating above a transition temperature. For example, a shape memory alloy wire can be formed into a memorized shape while in a high temperature austenitic phase. After cooling the shape memory wire to a martensitic state while maintaining the memorized shape, the wire may be plastically deformed to a different configuration in which it can be inserted into the delivery trochar. If the wire is deployed from the delivery tube at body temperature and transforms to the austenite state, the wire can return to the memorized shape.

The wires may be deployed by the inherent springiness of the wire loops, or simply deployed manually by unrolling using graspers, attached to a control member, or the like. In all cases, the wires are arranged in a suitable fashion within the isolation bag so as to allow easy access to the tissue mass to be inserted within the space defined or created by the wire loops.

Figure 3D:
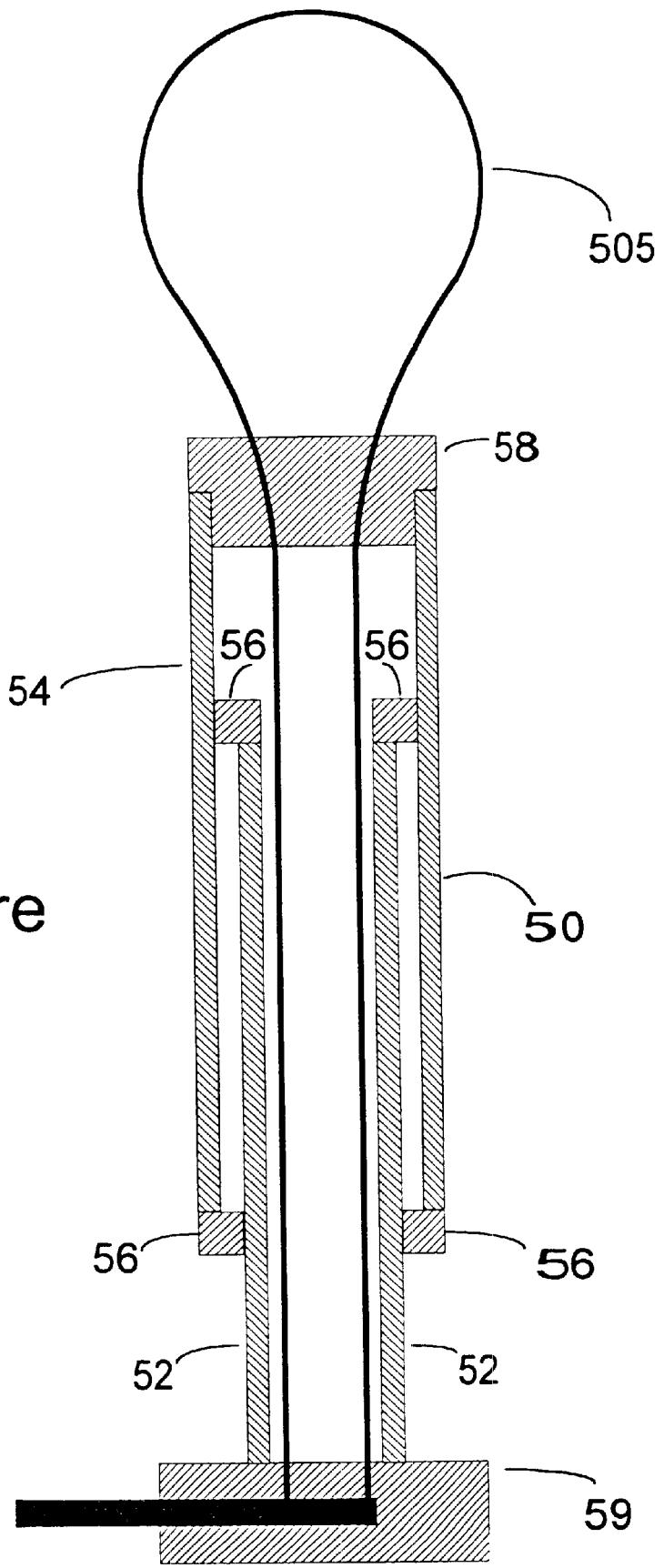
FIG. 3D is a cross sectional of one embodiment of a delivery trochar cannula.

In one embodiment as illustrated in FIG. 3D, delivery trochar 50 includes an inner tube 52 slidably received by an outer tube 54. The tubes are prevented from being overextended and separated by inner and outer insulated tube stops 56. The cage of wires 310 can be held in proper formation by a distal cap 58 of delivery trochar 50 while the ends of the wires pass through proximal insulated end 59 of delivery trochar. The cage of wires 310 can be easily resized, extended and retracted by an operator or surgeon by holding the outside of delivery trochar 50 with one hand and pushing or pulling proximal insulated end cap 59 which is connected to inner tube 52 into and out of outer tube 52 with the other hand.

In operation, the swing arms 320 and wire loop(s) 310 are deployed through delivery trochar 50. The tissue mass 10 would then be loaded into the cage created between wires 310 and outer surface 322 of swing arms 320. The wire loops 310 are then retracted, pressing the tissue mass 10 against the outer surfaces 322 of the swing arms 320.

While wire loops 310 are being drawn through trochar 50, a high frequency current is applied to outer surfaces 322 of swing arms 320 (and membranes 3234) and wire loops 310. A mechanical or tension force is created by the wires pressing against the tissue mass while being held by outer surfaces 322 of swing arms 320. The mechanical cutting of tissue mass 10 can be enhanced by varying the diameter of the wires used. It is preferred that the wires be as thin as possible for effective cutting while at the same time be strong enough not to break when the tension force is routinely applied to them.

The A/C current applied to the wires and outer surfaces 322 of swing arms 320 assists in cutting the tissue mass. Current is caused to flow through the tissue mass between the two poles created by wire loops 310 and the outer surfaces 322 of swing arms 310. The tissue mass is, therefore, electrically cut by heat and local vaporization where the wires contact the tissue mass.

Figure 3E:
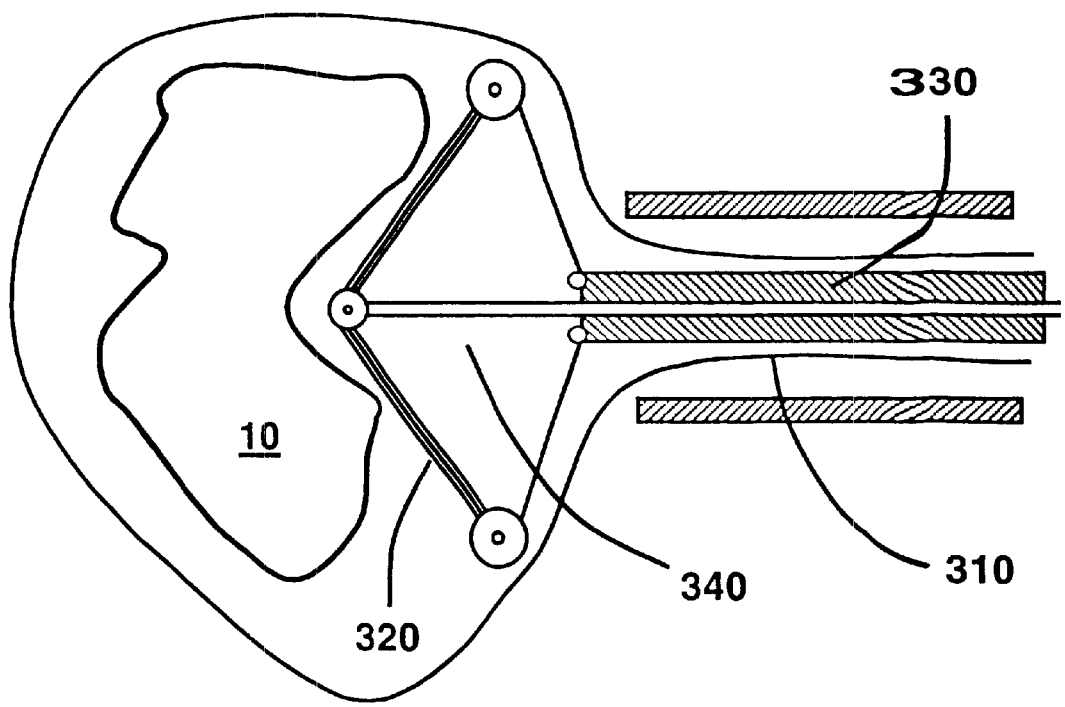
FIG. 3E is a cross sectional view of the invention with a push rod and independent swing arm assembly.

In one embodiment as shown in FIG. 3E, a push rod 340 may be used to push or deploy swing arms 320 or membranes 324 in a cone or similar shape configuration towards the tissue mass 10. Push rod 340 may receive current from generator 70. In this embodiment, the swing arms are independent from support shaft 330. The shape and configuration of the swing arms and membrane are determined and controlled by push rod 340.

After the tissue mass 10 has been reduced to smaller, thinner pieces, swing arms 320, support shaft 330 and wire loops 310 are withdrawn from bag 20 through delivery trochar 50. The delivery trochar 50 would also be removed through outer trochar 40. The thin pieces of tissue and isolation bag 20 are then removed from body cavity 30 using the methods as described above.

Figure 4B:
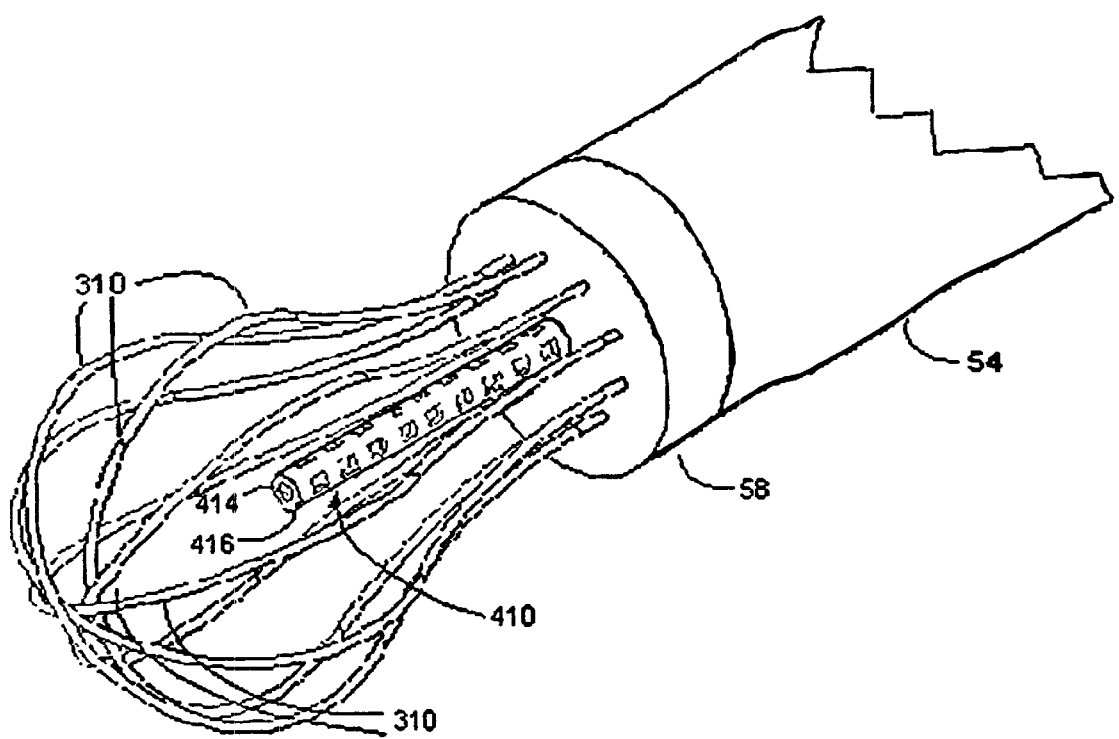
FIG. 4B is a perspective view detailing the cage of wires and center probe of the fourth embodiment of the invention.

In another example of the invention as shown in FIG. 4A, the swing arm assembly is replaced by a center rod 410. Center rod 410 is extended into the cage of wires by manipulating the insulator end 412 which extends out of the proximal insulated end cap 59 of delivery trochar 50.

The center rod 410 includes an exposed electrode 414 tightly surrounded by insulator end 412 and a center electrode fenestrated insulator 416. The fenestrated insulator 416 permits current to pass between the cage of wires and the center electrode while preventing the wires 310 from contacting center electrode 414. The center rod 410 can be constructed small enough in diameter to be capable of piercing the caged tissue mass.

In this embodiment, current is applied through the tissue mass 10 between center electrode 414 and the cage of wires 310. The outer electrode wires may be retracted in the same manner as described above to cut or reduce the tissue mass by a combination of mechanical and electrosurgical mechanisms while center rod 410 vaporizes, or alternatively, pierces the tissue mass 10.

Figure 5A:
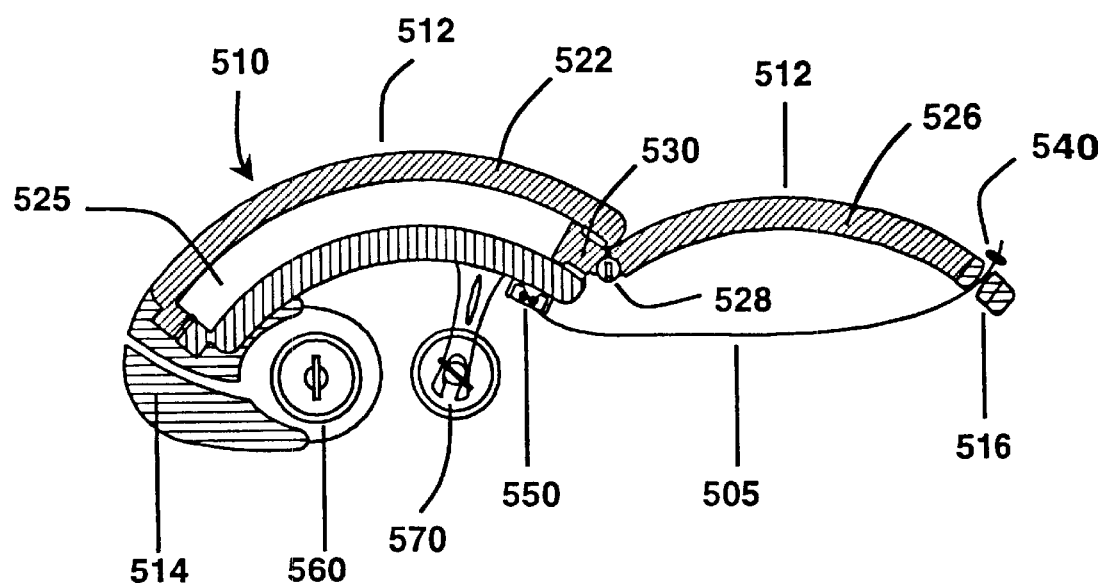
FIG. 5A is a top view of a fifth embodiment of the invention illustrating the wall and the wall extension.

In another embodiment of the invention, FIG. 5A illustrates a wall 510 deployable from delivery trochar 50. Wall 510 includes an outer conductive surface 512 facing the tissue mass 10 within isolation bag 20.

The outer conductive surface 512 of deployable wall 510 constitutes a first electrode that serves as one pole of a A/C circuit. At least one wire or ribbon loop 505, or alternatively, a wire cage assembly, constitutes a second electrode that serves as another pole of the A/C circuit.

The wall 510 also includes a left end cap wire guide 514 and a right end cap wire guide 516. These wire guides 514, 516 may be integrally formed with the wall or separate members attached or hingeably attached to the wall 510. The left and right wire guides 514, 516 serve as an electrical insulator and wire guide or support for the wire loops or cage assembly 505.

As shown in FIG. 5A, the wall 510 may include an inner portion 524 and an outer portion 522 defining a center space 525 for housing a wall extension 526. The wall extension 526 may be a single wall member that deploys out of one end of wall 510 and into isolation bag 20, increasing the effective surface area of outer conductive surface 512. Wall extension 526 is preferably made from the same electro-conductive material as the outer surface 512 of the wall 510 or, alternatively, from another electro-conductive material.

Figure 9:
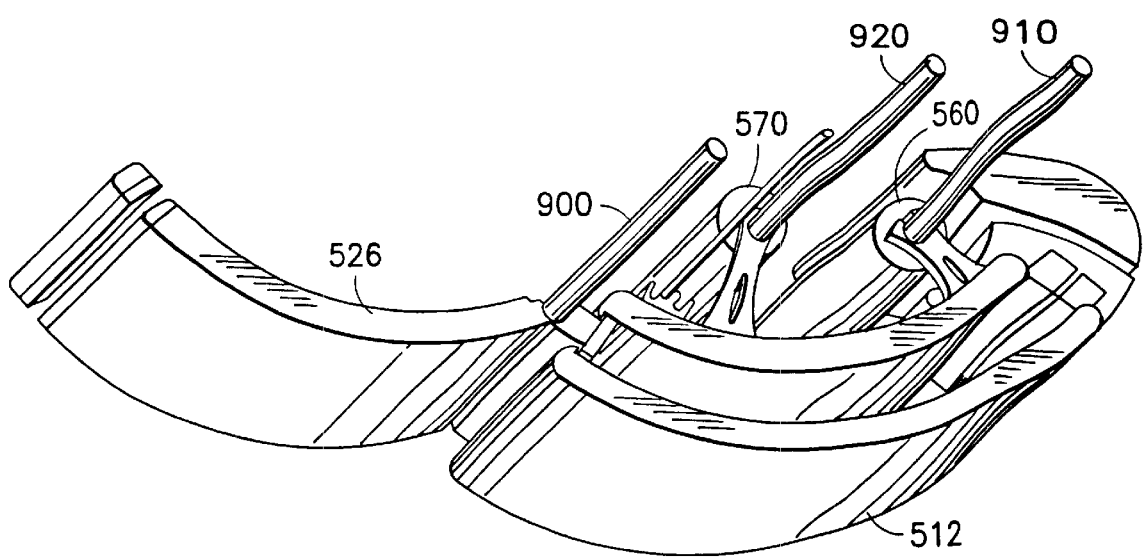
FIG. 9 is an perspective view of the fifth embodiment of the invention illustrating the control rods.

Wall extension 526 includes a hinge 528 and an anchor mechanism 530 to aid in positioning and locking wall extension 26 into place once it is fully deployed in isolation bag 10. Hinge 528 and anchor mechanism 530 may be adjusted or manipulated by a control rod (shown in FIG. 9) accessible by a surgeon. In the embodiment illustrated in FIG. 5A, the right end wire guide 516 is provided at the end or tip of wall extension 526.

It is to be understood that the wall 510 and wall extension 526, as used herein, can be any structure that forms a conductive outer surface, and are not limited to the crescent shape illustrated in the Figures.

Figure 6A:
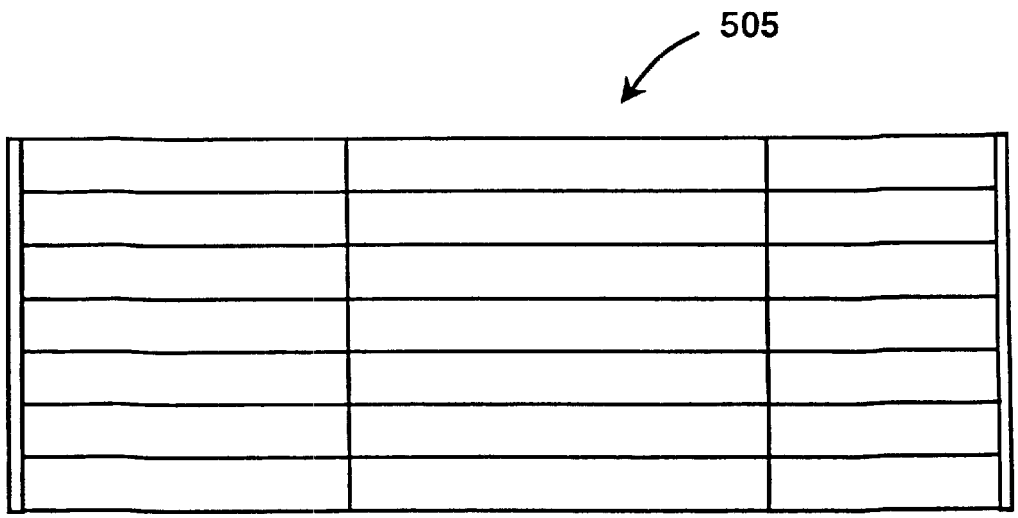
FIGS. 6A to 6D are side views of the wire grid assembly illustrating cross bracing.
Figure 6B:
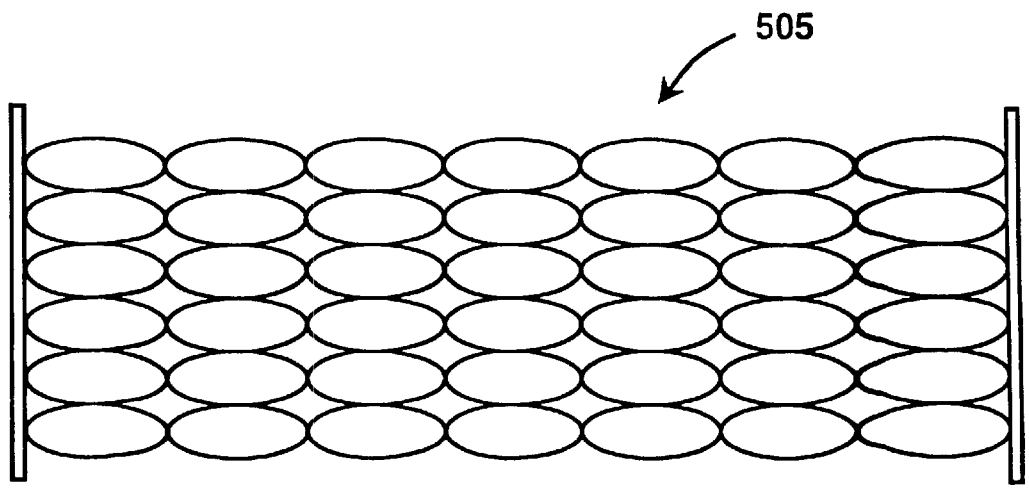

The wire grid assembly 505 is made of a plurality of thin, strong wires or ribbons. FIGS. 6A and 6B illustrate two possible configurations of the wire grid assembly having an outer boarder configured as a rectangle, although the wire grid assembly can be arranged in a variety of shapes and configurations.

Figure 6C:
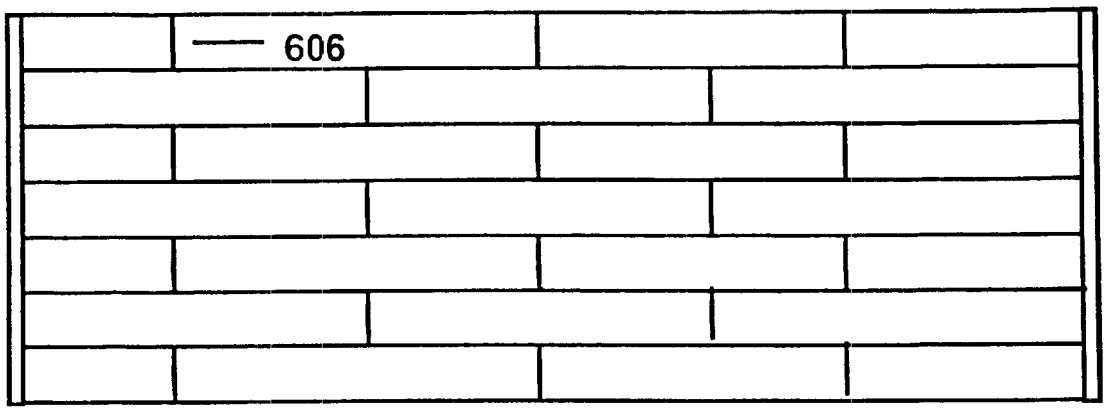
Figure 6D:
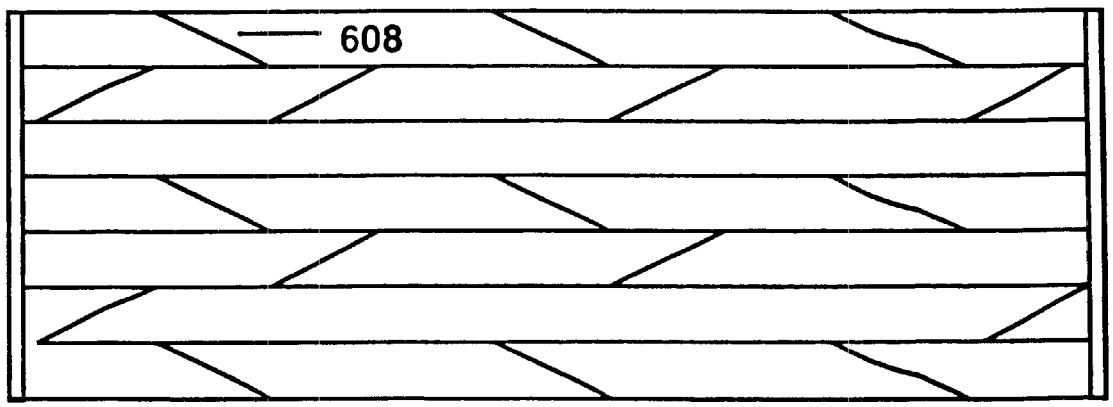
Figure 7A:
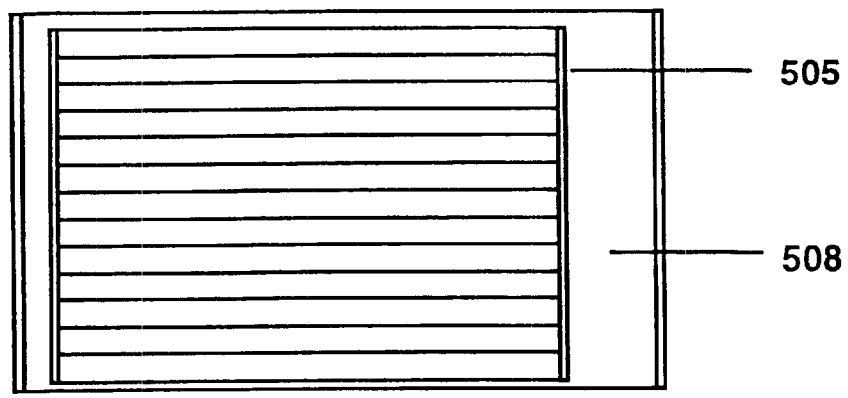
FIG. 7A is a side view of the wire grid assembly and sheet support.

FIGS. 6C and 6D illustrate various cross bracing configurations. The wires of the wire grid assembly may be uniformly spaced and arranged by the use of cross bracing 606, 608. Cross bracing 606, 608 may be fixed, permanent integral components of the wire grid and made from the same material as the wire grid. In an alternate embodiment, the cross bracing breaks away or falls off as the wire grid cuts into the tissue mass. The cross bracing may be made of a non-conducting material such as, for example, plastic, rubber composite or an organic material. The wire grid assembly 505 is supported on its outer periphery by a wire grid support sheet 508 (FIG. 7A). The support sheet 508 may be made of a pliable and strong sheet-like material such as, for example, plastic, rubber, teflon, or the like.

Figure 7B:
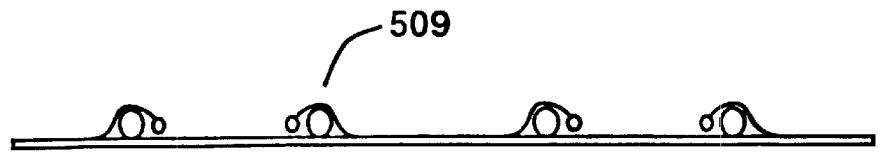
FIGS. 7B to 7D is a top view of the wire grid assembly and sheet support illustrating the attaching means of the wires to the sheet support.
Figure 7C:
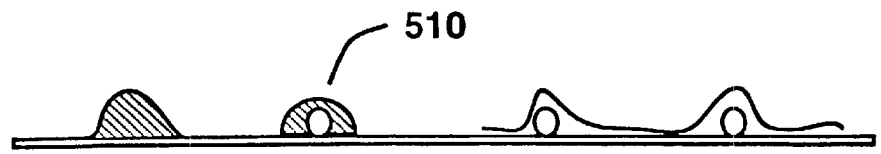
Figure 7D:
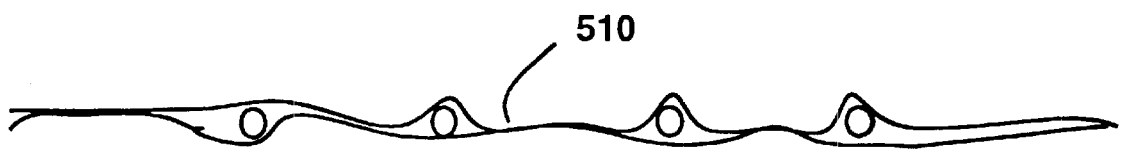

The wire grid 505 is attached to the support sheet 508 by, for example, small pliable hooks 509, glue 510, thin membranes 511, or imbedded groove channels (FIGS. 7B, 7C, 7D). As will be described in more detail below, the wires of the wire assembly easily release or detach from the support sheet 508 as the wires cut deeper into the tissue mass 10.

In an alternate embodiment, support sheet 508 is a membrane support. The membrane support would break up into very small pieces as the wire grid breaks, tears or detaches from the membrane support.

Referring back to FIG. 5A, wire grid assembly 505, at one end, includes an anchor block 540 which is attached to an anchor strip 550 mounted on inner surface 524 of the wall 510. The other end of the wire grid assembly passes through right wire guide 516 defined in wall extension 526, around tissue mass 10, through right wire guide 514, and onto a first roller 560. First roller 560 is mounted onto inner portion 524 of wall 510.

A first end of wire grid support sheet 508 includes an anchor block 540 which is also attached to anchor strip 550 mounted on inner surface 524 of wall 510. The second end of wire grid support sheet 508 is sent around the tip or end 516 of wall extension 526, around wire grid assembly 505, around closed other end of wall 510 and onto a second roller 560. Second roller 570 is also mounted on inner portion 524 of wall 510 by a bracket 572.

Figure 8A:
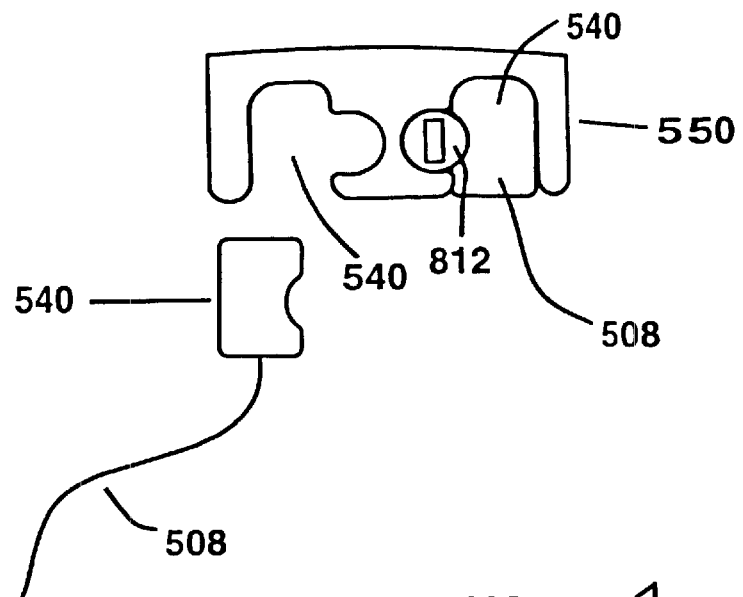
FIG. 8A is a top view of one means for attaching the wire grid assembly, support sheet or isolation bag by using an anchor strip and anchor blocks.

As illustrated in FIG. 8A, the anchor strip 550 for attaching the wire grid assembly 505 and support sheet 502 to inner surface 524 of wall 510 includes a receptacles 810 for receiving anchor blocks 540 of wire grid assembly 505 and support sheet 508. Retaining pins 812 lock anchor blocks 540 to anchor strip 550. The retaining pins 812 are capable of being removed remotely through delivery trochar 50. This provides a surgeon the ability to disassemble the device from the outside of the body and facilitates the removal of the various components, as well as to address any difficulties that may arise during the procedure. It should be understood that other means of attaching the ends of the wire grid assembly and the wire support may be used.

Figure 8B:
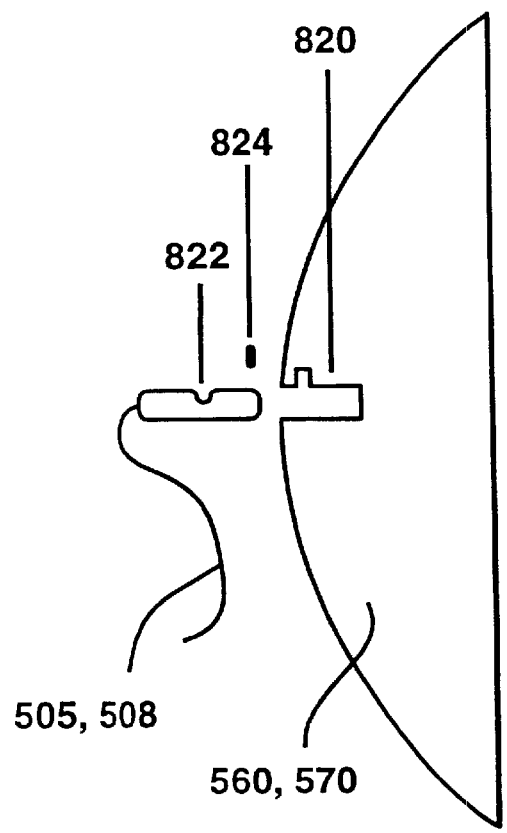
FIG. 8B is a top view of one means for attaching the ends of the wire grid assembly, support sheet or isolation bag to the rollers.

The other ends of wire grid 505 and sheet support 508 are coupled to first and second rollers 560, 570, respectively, as shown in FIG. 8B. A recess 820 in the rollers receives an anchor block 822, which is held by retaining pin 824.

Figure 5B:
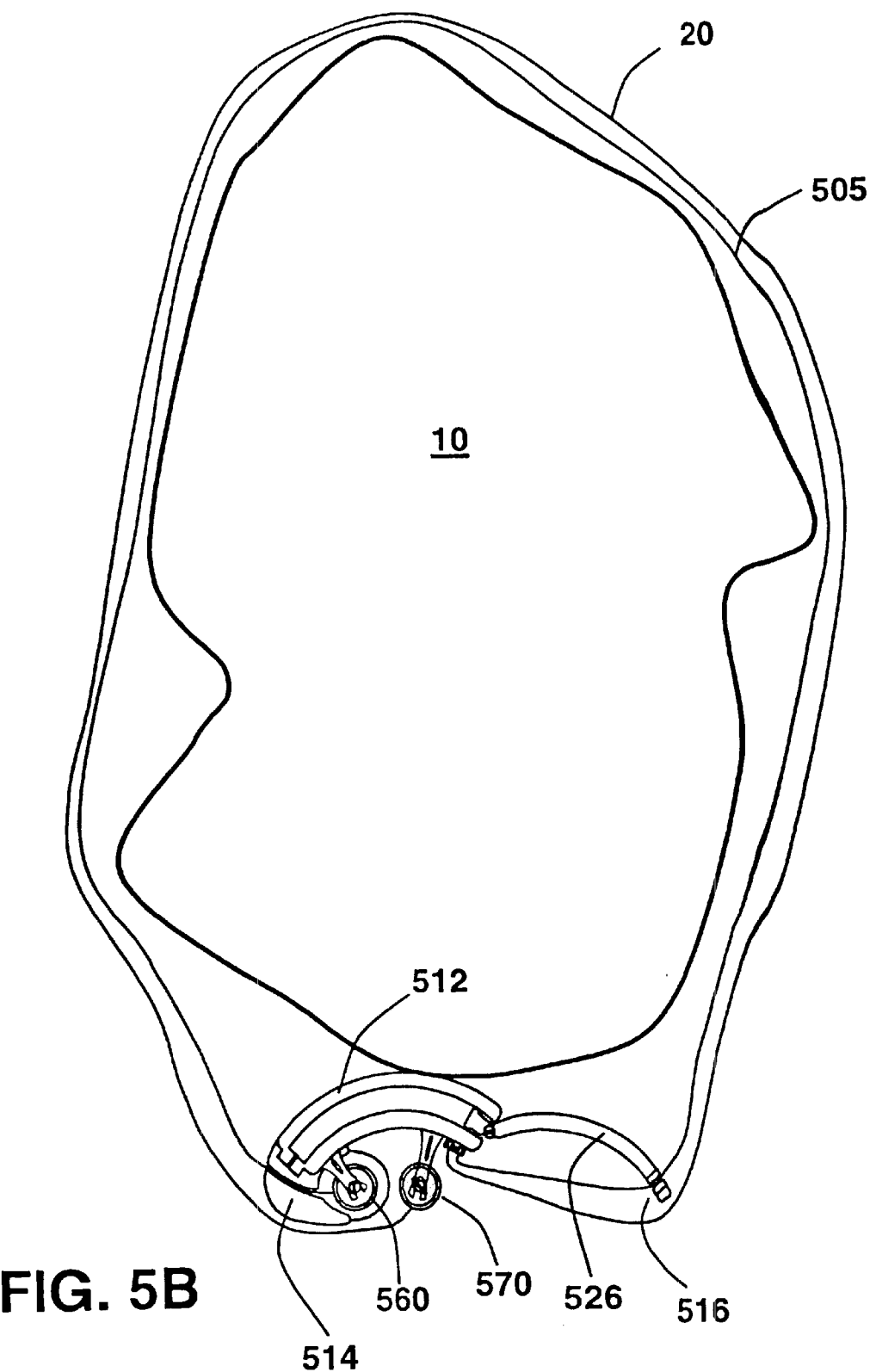
FIGS. 5B and 5C are cross section views illustrating the operation of the fifth embodiment.
Figure 5C:
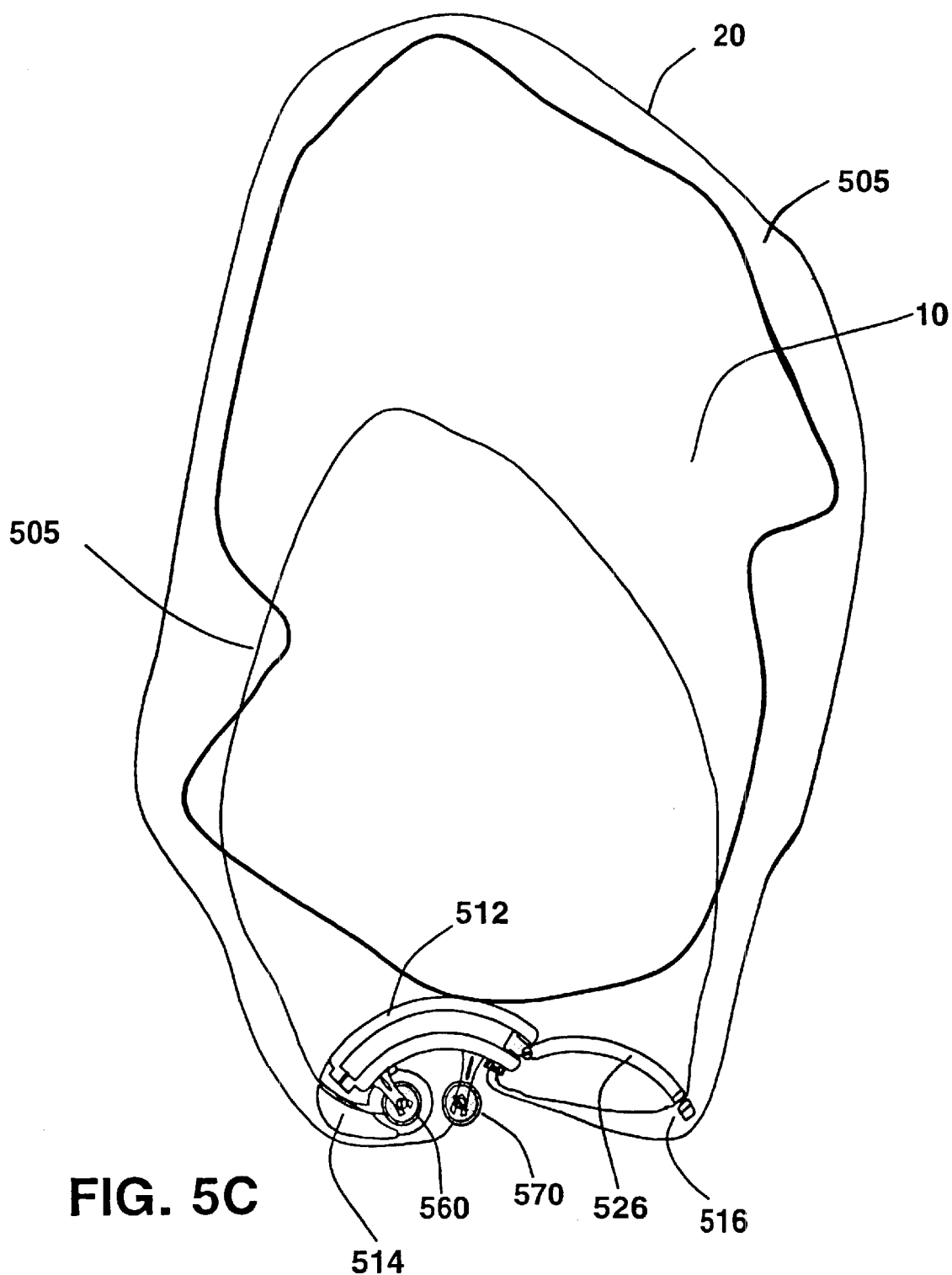

In operation, tissue mass 10 is brought into the interior space defined by wire grid assembly 505 and outer surfaces 512 of wall 510 and wall extension 526 by manipulating surgical forceps or tweezers commonly used during surgery or, alternatively, intrinsic engineering to perform this procedure. (FIGS. 5B, 5C) In one embodiment, the forceps or tweezers have an integrated camera system for maximum control.

The tissue mass 10 that has been placed between outer surfaces 512 of wall 510 and wall extension 526 and wire grid assembly 505 forms an electrical path or circuit between outer surfaces 512 and wires 505 (i.e. two poles of the generator). Current is fed to outer surfaces 512 of wall 510 and wall extension 526 through wires coupled directly to the A/C generator 70. In an alternate embodiment, current is fed through a control rod 900 controlling hinge 528 of the wall extension (see FIG. 9). Current may also be fed to the first roller 560, which is connected to the wires of the wire grid assembly 505, through a second control rod 910. In an alternate embodiment, current is fed directly from the A/C generator 70 to the first roller 560 or the wire grid assembly 505.

The tissue mass 10 is then cut by a combination of mechanical and electro-surgical means. First roller 560 is turned by, for example, control rod 910, in order to tighten wire grid assembly 505 against tissue mass 10. Tension is created to mechanically cut the tissue mass by the turning of roller 560 as wire grid 505 is reeled or spooled onto roller 560. The current applied to wires 505 and outer surfaces 512 of wall 510 and wall extension 526 assist in cutting the tissue by heat and local vaporization where the wires contact the tissue mass.

As the wires cut through the tissue mass, they release from support sheet 508, while support sheet 508 remains on the outer surface of the cut tissue mass. The support sheet 508 is then reeled or spooled onto second roller 570. In the embodiment in which a membrane support is used, there is no need to reel the membrane support onto a second roller because the membrane would break up into many small pieces and remain on the outer surfaces of the tissue mass.

Figure 10A:
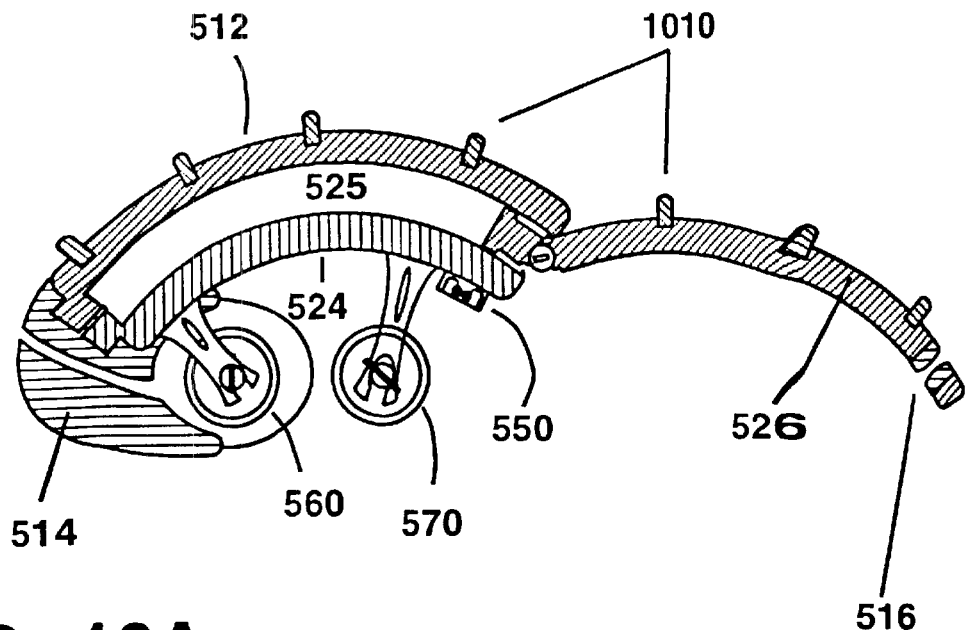
FIG. 10A is a cross sectional view of one embodiment of the invention illustrating optional insulating members attached to the outer surface of the wall and wall extension.
Figure 10B:
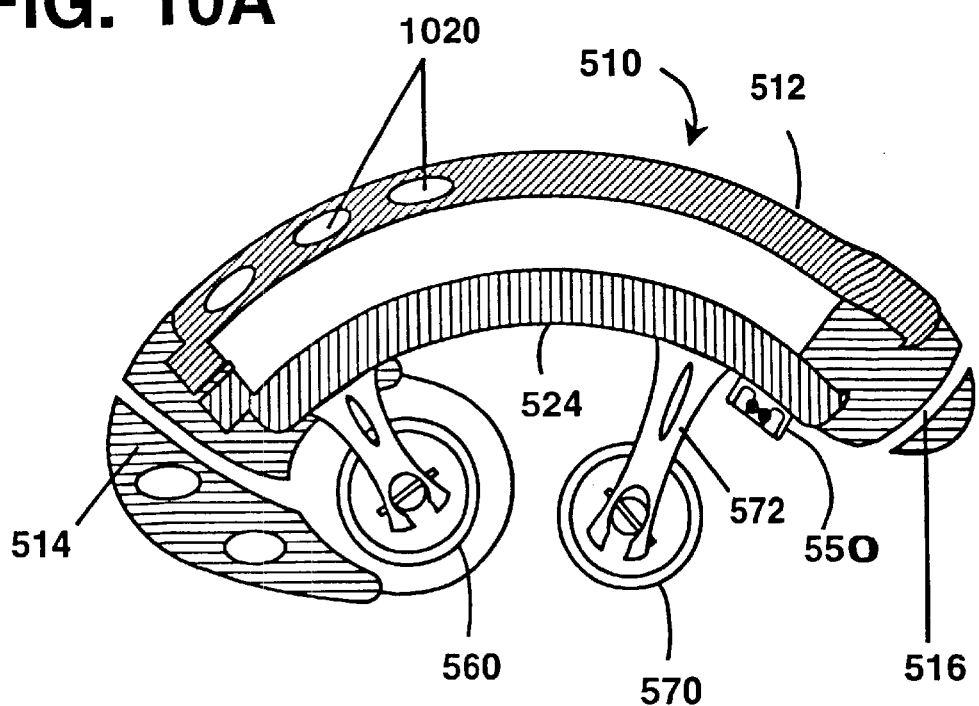
FIG. 10B is a cross section view of one embodiment of the invention illustrating cooling channels passing through the wall.

In one embodiment, small insulating inserts 1010 are placed along outer surfaces 512 of wall 510 and wall extension 526 to prevent grounding or shorting of the wires upon direct contact with the outer surfaces (FIG. 10A). The inserts 1010 may be placed at approximately 90 degree angles to the main axis of the wires of the wire grid assembly. The wall 50 may also incorporate coolant channels 1020 circulating cooling fluid through the surgical instrument assembly (FIG. 10B).

Once the tissue mass has been cut and the wire grid has been reeled onto first roller 560, wall extension 526 is inserted back into opening 525 defined by the inner and outer portions 524, 522 of wall 510 by control rod 900. The wall 510 is then removed from isolation bag 20 through delivery trochar 50. The thin pieces of tissue are then removed in the same manner as described above.

In another example of the invention, FIG. 11 illustrates alternative docking or locking mechanisms for wire grid assembly 505 and isolation bag 1105 (or wire grid support sheet 508) to wall 510 or, alternatively, wall extension 526.

In this example, wire grid assembly 505 includes a first end having a male member 110 and a second end attached to a first spool 1120. The isolation bag 1102 includes a proximal end having a male member 1130 and a distal end attached to a second spool 1140.

As shown in FIG. 11, male member 1130 of isolation bag 20 is docked into an insulated end dock 1150 attached to inner portion 524 of wall 510 or, alternatively, formed integral to the inner portion. The insulated end dock 1150 defines a U-shaped recess 1152 for receiving male member 1130 of isolation bag 1105. The male member 1130 is held or locked together with U-shaped recess 1152 of insulated end dock 1150 by restricting or locking members 1154. The first spool may be docked or attached to left end cap 514 of the wall 410 or, alternatively, by a bracket attached to inner portion 524 of wall 510.

The male member 1110 of the wire grid assembly 505 and second spool 1140 holding the distal end of the isolation bag 1105 are a combination assembly that are held together by a "U" shaped recess defined in the spool. Male member 1110 of the wire grid assembly is held or locked together with second spool 1140 by restricting or locking members 1152. The combination assembly is docked or attached to the right end cap 516 of the wall 510, or, in alternate embodiments, the wall extension 526.

In this embodiment, isolation bag 1105 is deployed on the outside of wire grid assembly 505 to prevent electrical or thermal damage to the body cavity. It is preferred that the deployed bag include an insulated shroud (not shown) that is continuous with the upper part of the device that can be brought out over the outside of the laparoscopic opening to keep the inside of the bag electrically insulated from the patient. In an alternate embodiment, the shroud can be detachable from the bag.

Once bag 1105 is fully deployed to surround the tissue mass 10 inside body cavity 13, first spool 1120 is capable of being rotated by, for example, a control rod, to reel the wire grid assembly thereon so as to reduce the space defined by wire grid assembly 505 with outer surface 512 of wall 510. Similar to the devices described above, the tissue mass is reduced or vaporized by a combination of mechanical and electro-surgical mechanisms.

After the tissue mass has been reduced to thinner, smaller pieces, the current is no longer supplied to the outer surface of the wall. Male members 110, 1130 and spools 1120, 1140 are undocked, rolled up and removed through delivery trochar 50.

Figure 12A:
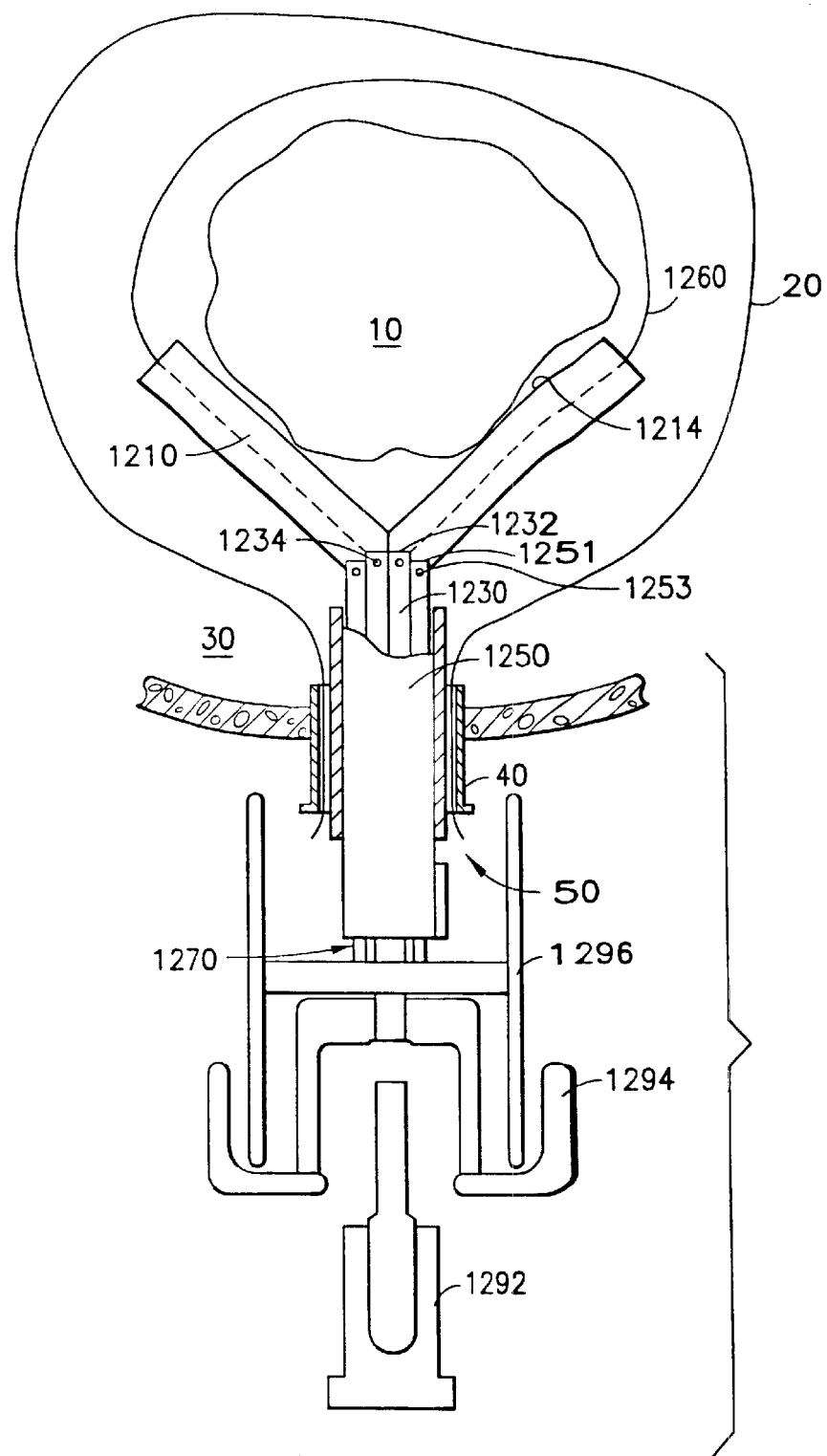
FIG. 12A is a side view of another embodiment of the invention illustrating a inner control rod, a outer control rod and a wire extension.

FIG. 12A illustrates another device using both mechanical and electro-surgical mechanisms to reduce the tissue mass 10 into smaller pieces within isolation bag 20. The device includes four swing arms 1210, 1220 deployed or controlled by an inner control rod 1230 and an outer control rod 1250. It is understood that the device may include less than or more than four swing arms.

Figure 12B:
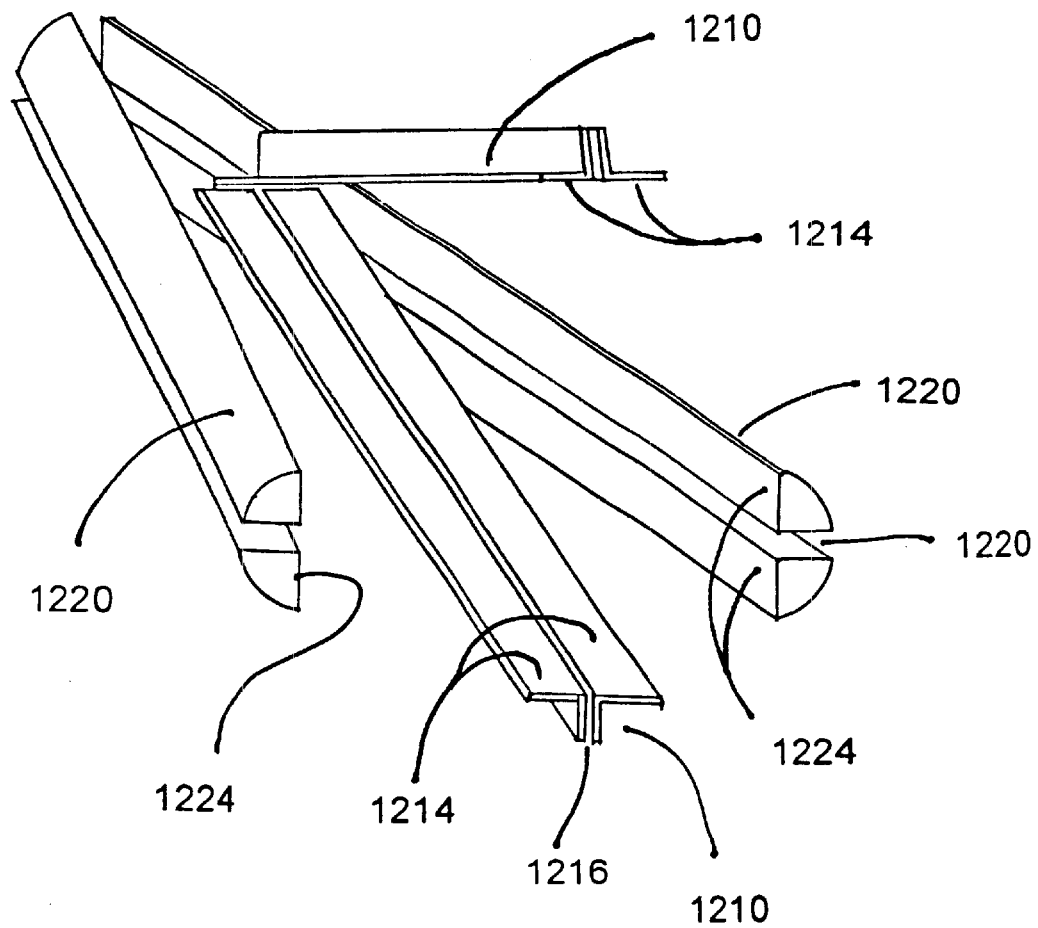
FIG. 12B is a perspective view of one embodiment illustrating the deployment of D-shaped and T-shaped swing arms.
Figure 12C:
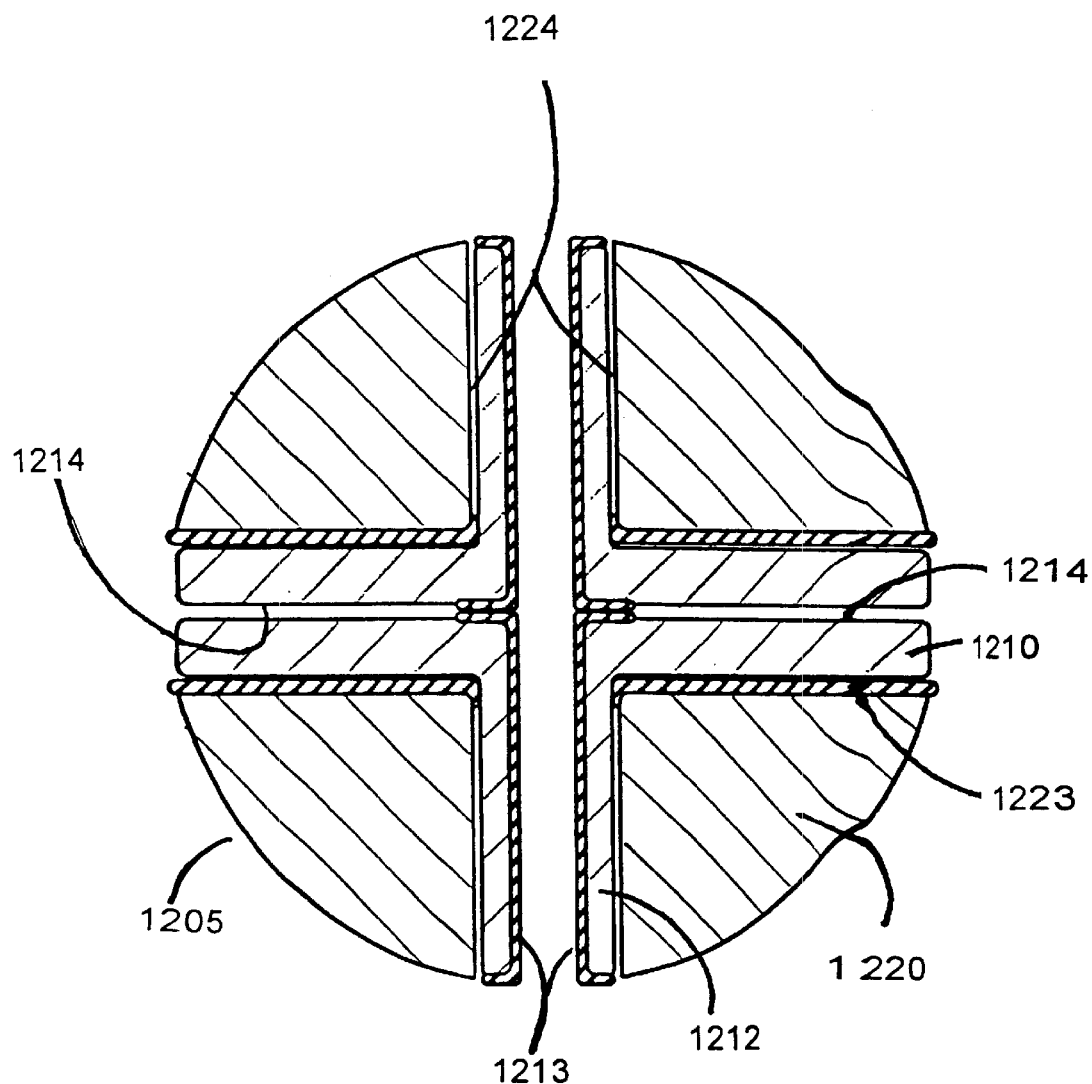
FIG. 12C is an end view illustrating D-shaped and T-shaped swing arms in an undeployed position.

As shown in FIGS. 12B and 12C, swing arms 1210 are T-shaped and swing arms 1220 are D-shaped. Swing arms 1220 have a recess or channel 1222, preferably lined with a non-conductive material (liner 1223), for receiving base 1212 of T-shaped swing arms 1210 while in the undeployed or stored position. The swing arms 1210, 1220, while in an undeployed position (FIG. 12C), are nested or fit together to minimize the diameter or outer dimensional size 1205 created by the undeployed swing arms 1210, 1220. The swing arms 1210, 1220 in the undeployed position are capable of fitting through a smaller delivery trochar than the delivery trochar required for the swing arm assembly illustrated in FIG. 3A.

While in a deployed position (FIG. 12B), the swing arms 1210, 1220 of this embodiment provide a greater surface area than the swing arms shown in FIG. 3A, facing tissue mass 10. The swing arms 1210, 1220 are pivotably secured to proximal ends 1232, 1251 of inter control rod 1230 and outer control rod 1250 by pivots 1234, 1253, respectively.

Similar to swing arms 320 illustrated in FIG. 3A, each swing arm 1210, 1220 includes an outer conductive surface 1214, 1224, respectively, facing tissue mass 10 while fully extended in isolation bag 20. The outer surfaces 1214, 1224 are coupled to A/C generator 70 by wires (not shown). These wires may pass through a plurality of bores or holes 1236 going through inner control rod 1230. The outer conductive surfaces 1214, 1224 constitute a first electrode that serves as one pole of an A/C circuit. In an alternate embodiment, outer surfaces 1214, 1224 of the swing arms 1210, 1220, respectively include a plurality of electrodes individually connected to the A/C generator. The remaining portions of swing arms 1210, 1220 are preferably made from an insulated or non-conductive material.

Figure 12D:
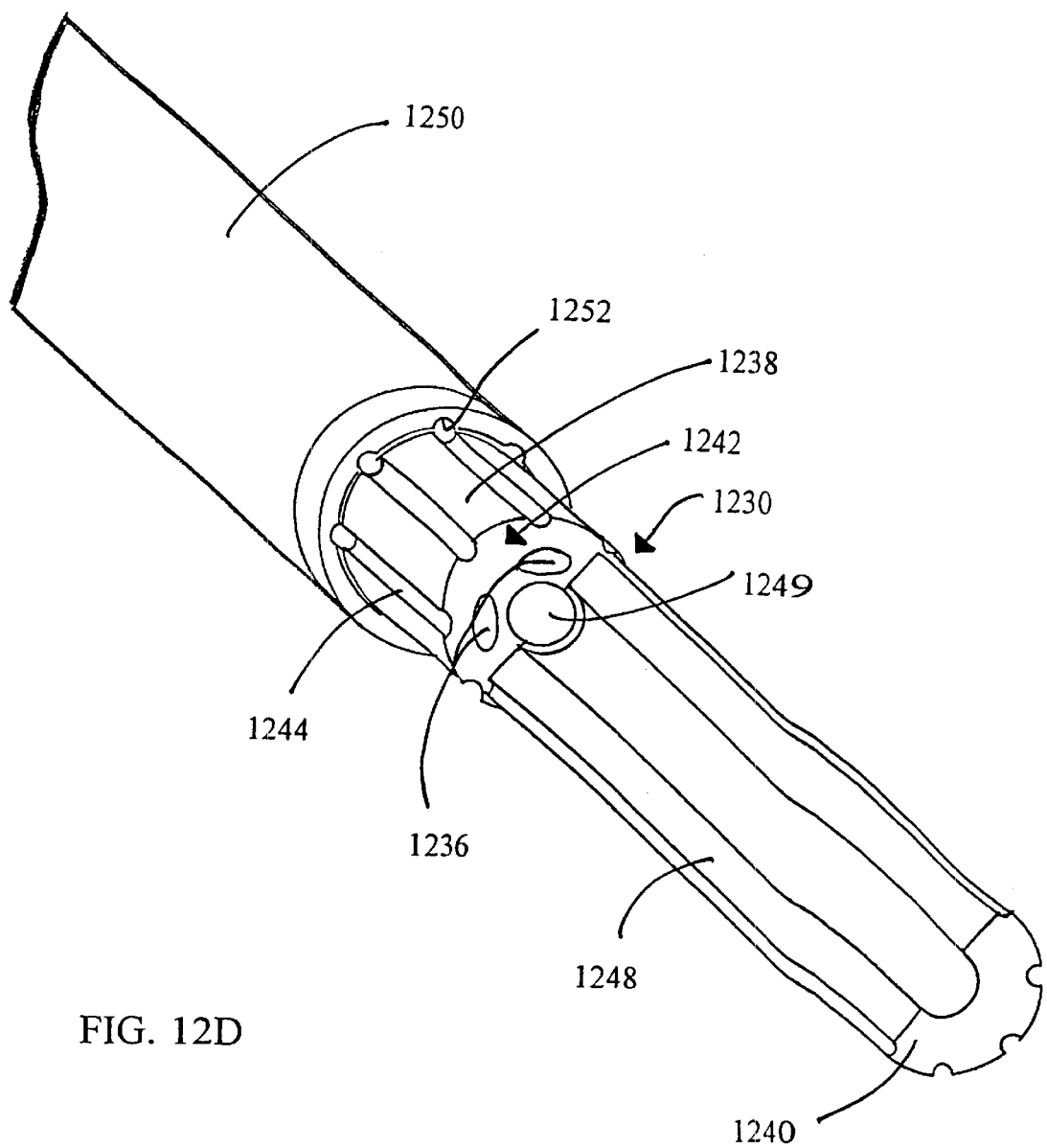
FIG. 12D is a perspective view of an inner control rod slidably received by an outer control rod.

As shown in FIG. 12D, the outer control rod 1250 is an elongated tube having a plurality of grooves, channels or recesses 1252 defined in the inner surface 1254 extending parallel with respect to each other. The outer control rod 1250 slidably receives inner control rod 1230.

The inner control rod 1230 includes an elongated rod 1238 and a C-shaped backbone member 1240 protruding from distal end 1242 of elongated rod 1238. As mentioned above, bores or holes 1236 pass through the elongated rod 1238. These recesses 1236 may serve as a conduit for wires that supply current to the conductive surfaces of swing arms 1210, 1220 or, alternatively, may serve as access ports for thermal or other data sensors, irrigation, or the like.

Figure 12E:
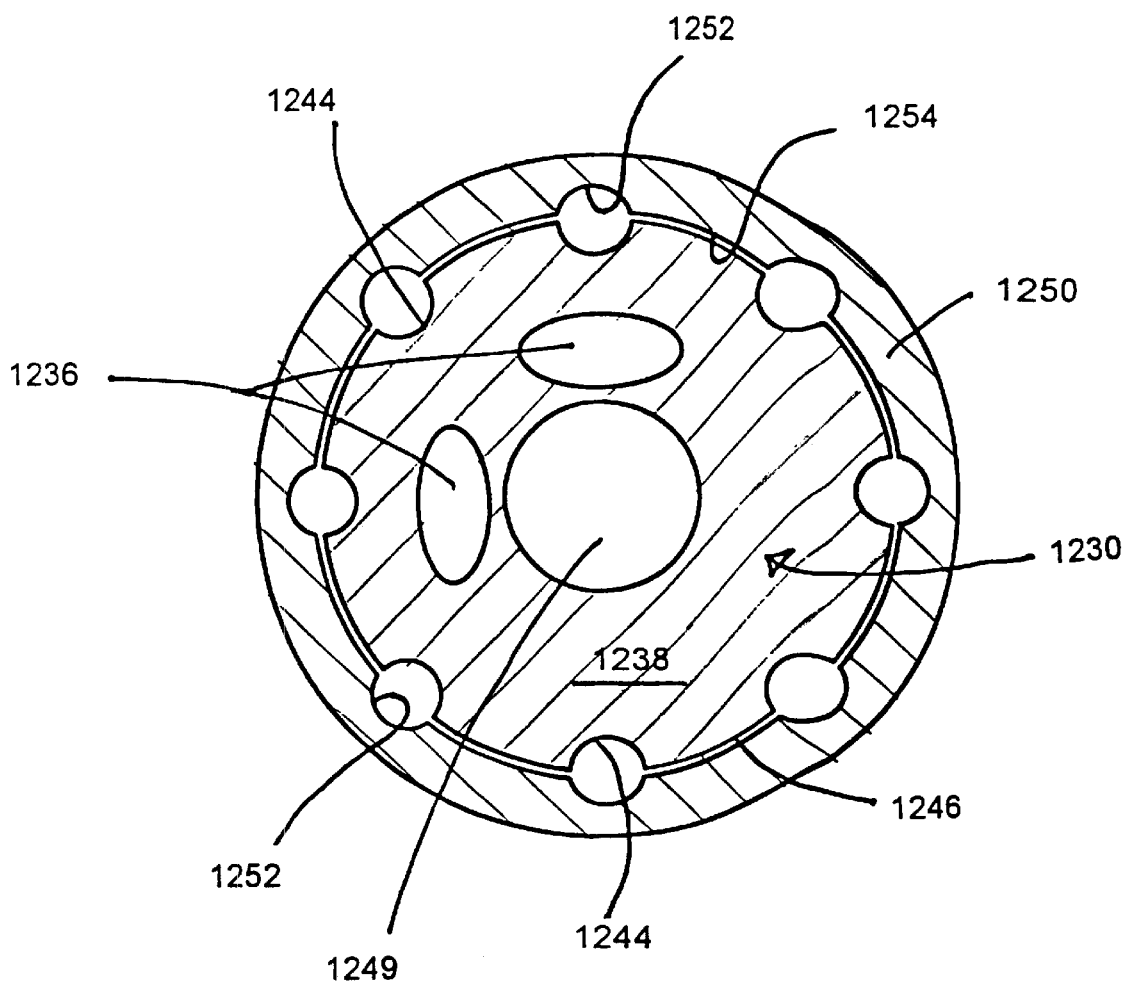
FIG. 12E is a cross-sectional view of one embodiment illustrating aligned grooves formed in an outer control rod and an inner control rod.

A plurality of grooves, channels or recesses 1244 are formed in outer surface 1246 of elongated rod 1238. These grooves 1244 align with grooves 1252 formed in inner surface 1254 of outer control rod 1250 when inner control rod 1230 is inserted into outer control rod 1250 (FIG. 12E). In one embodiment, a key member (not shown) protruding from the outer surface of the elongated rod fits into a recess or channel (not shown) in inner surface 1254 of outer control rod 1250 to ensure that grooves 1252 and 1244 are properly aligned. However, any alignment means used and known in the art for this purpose can be used.

The inner and outer control rods 1230, 1250 provide mechanical actuation of swing arms 1210, 1220 and other components by changing the relative position of inner and outer control rods 1230, 1250 with respect to each other, as will be discussed in more detail below. The inner and outer control rods 1230, 1250 also provide physical or mechanical support for swing arms 1210, 1220 allowing the swing arms to resist the mechanical forces created as wires 1260 slice through tissue mass 10 while, at the same time, pressing tissue mass 10 against conducting surfaces 1214, 1224 of swing arms 1210, 1220. Preferably, inner and outer control rods 1230, 1250 are made from an insulated or non-conductive material.

The aligned grooves 1252, 1244 formed in outer and inner control rods 150, 1230, respectively serve as a guide or conduit for a plurality of wires 1260 that form a loop or, in alternate embodiments, an egg-beater configuration, within isolation bag 20. The function, structure and composition of the wire loops are similar to wire cage 505 described above. The wires are separated from each other by the aligned grooves 1244, 1252, preventing a short from occurring (FIG. 12G).

As shown in FIG. 12B, slits or channels 1216, 1226 are defined in the non-conductive portion of swing arms 1210, 1220, respectively. The slits 1216, 1226 serve as wire guides for the wires constituting the wire loop or cage 1260 deployed into isolation bag 20. These slits 1216, 1226 aid in supporting the structure of wire loop or cage 1260. The swing arms 1210, 1220 may include a cap or other stop means (not shown) at the ends extending into isolation bag 20 to prevent the wires from falling out of the slits 1216, 1226.

In operation, the wires would pass through grooves 1244, 1252 defined in inner and outer control rods 1230, 1250, respectively, over pivots 1234 pivotably connecting the swing arms to inner control rod 1230, through slits 1216, 1226 defined in the swing arms 1210, 1220, respectively, and into isolation bag 20 to form a loop or cage so that tissue mass 10 can be inserted into. The surfaces of the swing arms defining slits 1216, 1226 are lined with a non-conductive material (liners 1213, 1223) to isolate the wires from conductive surfaces 1214, 1224, that a short circuit is avoided.

Figure 12F:
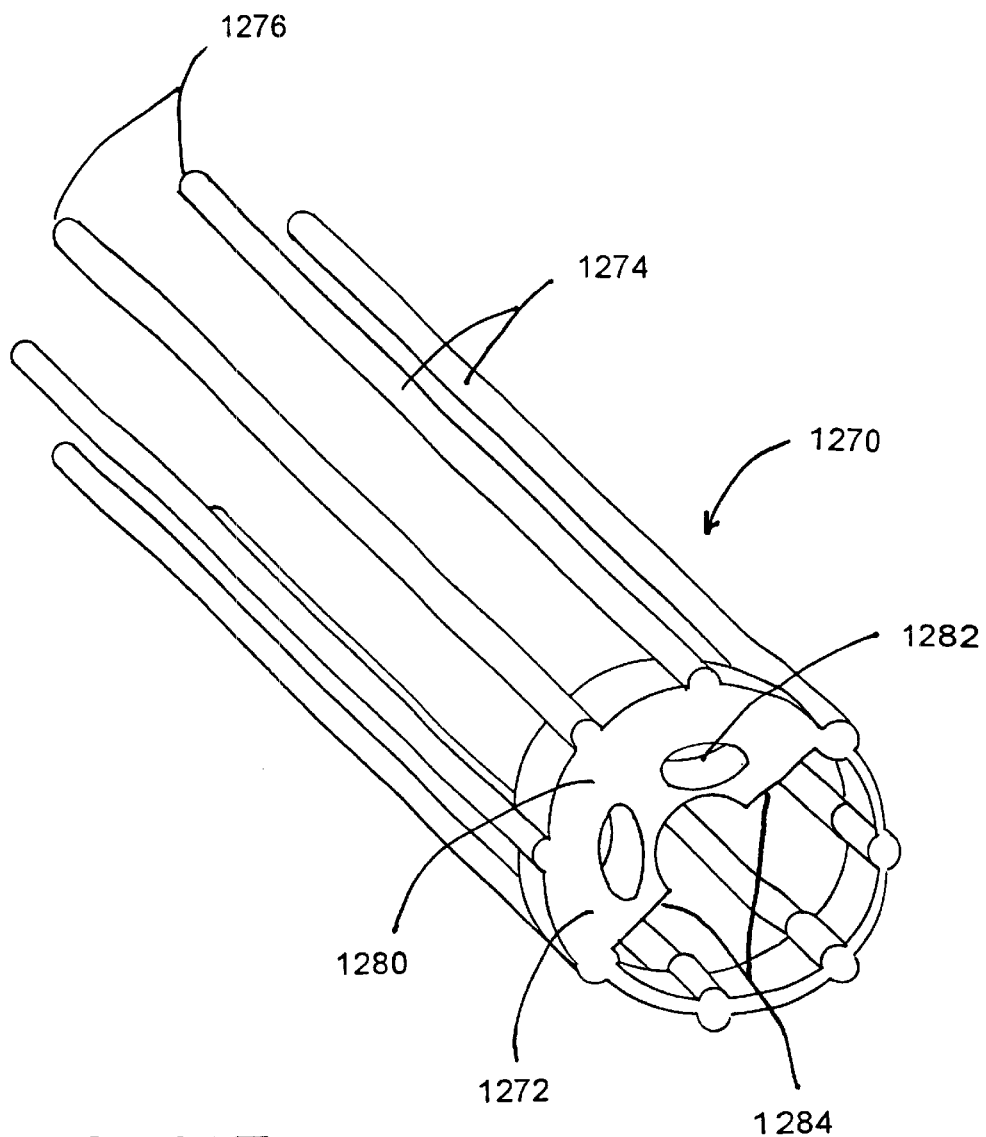
FIG. 12F is a perspective view of a wire extension.
Figure 12G:
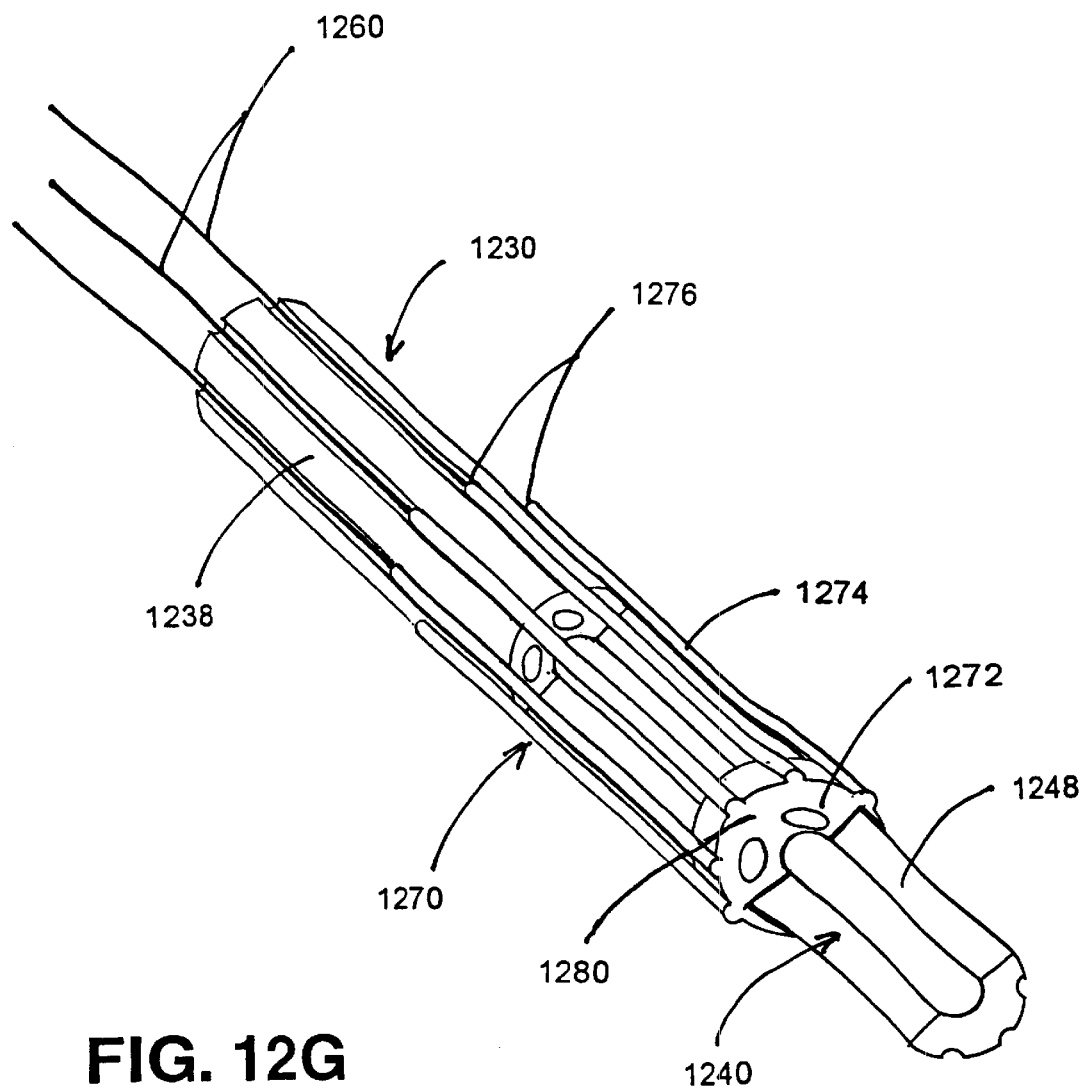
FIG. 12G is a perspective view of a mating contact between a wire extension and a backbone member of a inner control rod.

In one embodiment as shown in FIGS. 12F and 12G, a wire deployment rack 1270 is utilized to improve the control of the wires and shorten the wires used to segment tissue mass 10. The wire deployment rack 1270 includes base member 1272 having a plurality of elongated wire extensions 1274 extending from base member 1272. The wire extensions 1274 are positioned parallel with respect to each other and are dimensioned to be slidably received by the aligned grooves 1244, 1252 formed in the inner and outer control rods 1230, 1250, respectively.

The ends of the wires used to form the loop 1260 or, alternatively, the egg-beater configuration, are attached by soldering, compression fitting, or other means known in the art, to the distal ends 1276 of the wire extensions 1274 Alternatively, the wire extensions 1274 may include holes for receiving the wires. The wire extensions 1274 effectively decrease the length of the wires used to segment tissue mass 10. The shorter the wires used, the less likely that the wire will break during a procedure.

The wire deployment rack 1270 also allows the attachment point of distal end 1276 of wire extensions 1274 and the wires 1260 to be as close as possible to ends 1232, 1251 of inner and outer control rods 1220, 1250, respectively, when fully deployed. This improves the control of the wires by avoiding the snagging, binding up or tangling of the wires while in aligned grooves 1244, 1252.

Current is supplied from A/C generator 70 directly to wire extensions 1274. The current passes through distal ends 1276 to wires 1260. As discussed above, an electrical path or circuit is then created between wires 1260 and conductive surfaces 1214, 1216 of swing arms 1210, 1220, respectively, through tissue mass 10. The current is used to aid in segmenting or reducing the tissue mass by an electro-surgical mechanisms (e.g. cutting and coagulation).

As shown in FIGS. 12F and 12G, base member 1272 of wire deployment rack 1270 includes an outer ring 1278 and a C-shaped member 1280 attached to outer ring 1278. The outer ring 1278 supports wire extensions 1274. The C-shaped member 1280 includes two recesses or bores 1282. Recesses 1282 align with the bores or holes 1236 passing through elongated rod 1238 when the device is fully assembled and in operation. A guiding surface 1284 of C-shaped member 1280 is slidably received by a guiding surface 1248 of C-shaped backbone member 1240 of inner control rod 1230. When wire extensions 1274 are introduced into aligned grooves 1244, 1252 formed in inner and outer control rods 1230, 1250, respectively, the mating contact of guiding surface 1248 of C-shaped backbone member 1240 and guiding surface 1284 of the C-shaped member 1280 of base member 1272 ensures that the recesses 1282 properly align with bores or holes 1236 passing through elongated rod 1238 of inner control rod 1230.

Figure 12H:
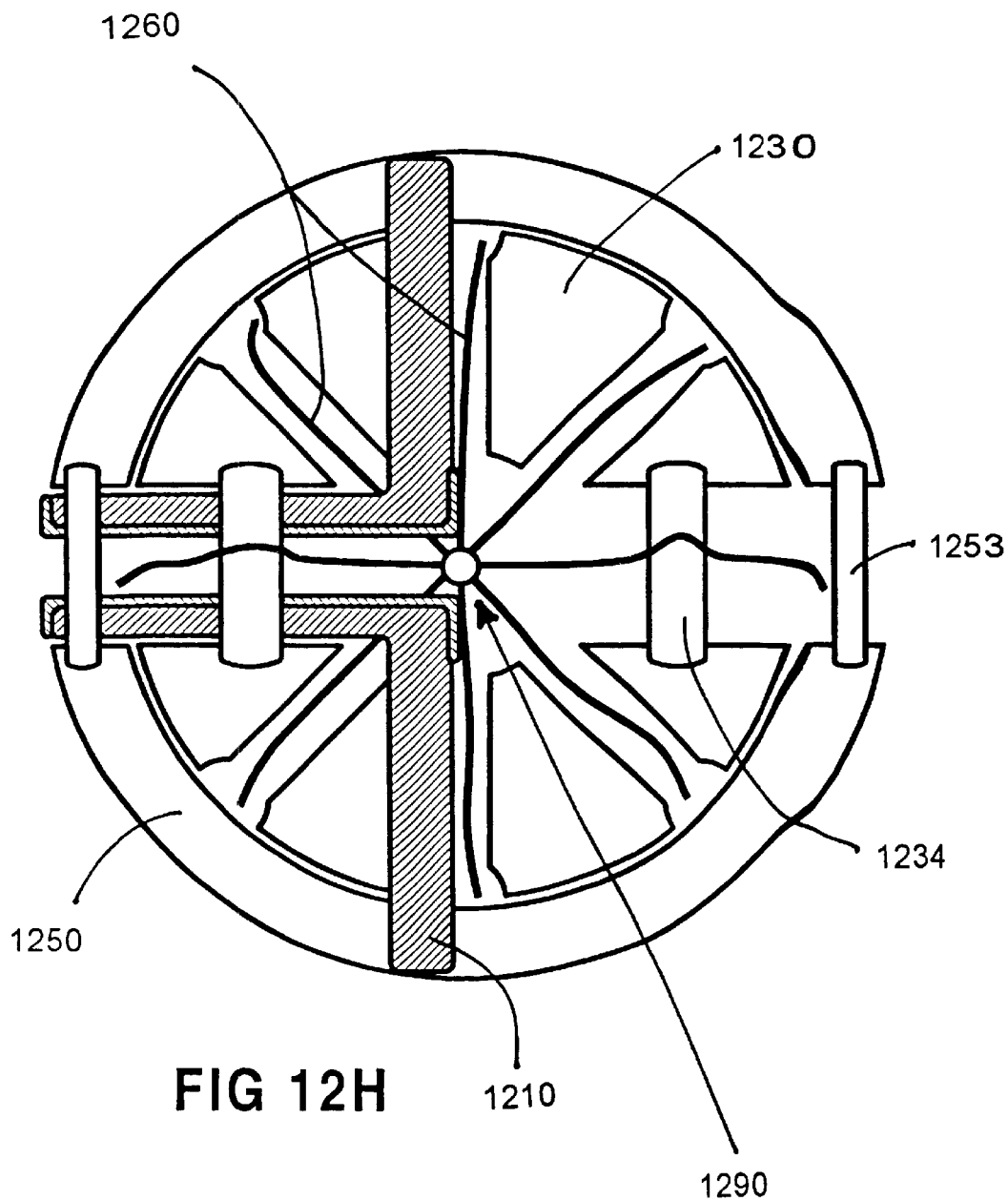
FIG. 12H is a cross-sectional view of one embodiment illustrating a wire end control point button.

In one embodiment as illustrated in FIG. 12H, the wire loops maintain its egg-beater configuration by a wire control point button 1290 coupling or holding together the apex of each loop 1260 to each other. In this example, a button control rod 1292, illustrated in FIG. 12A, may be used to control the positioning of wire control point button 1290. The button control rod 1292 may extend from outside of the body cavity (controlled by a surgeon) and through a center bore or hole 1249 defined by elongated rod 1238 of inner control rod 1230. The button control rod 1292 may include a hook, snare, or the like (not shown) at a distal end to aid in manipulating the control point button 1290.

Figure 12I:
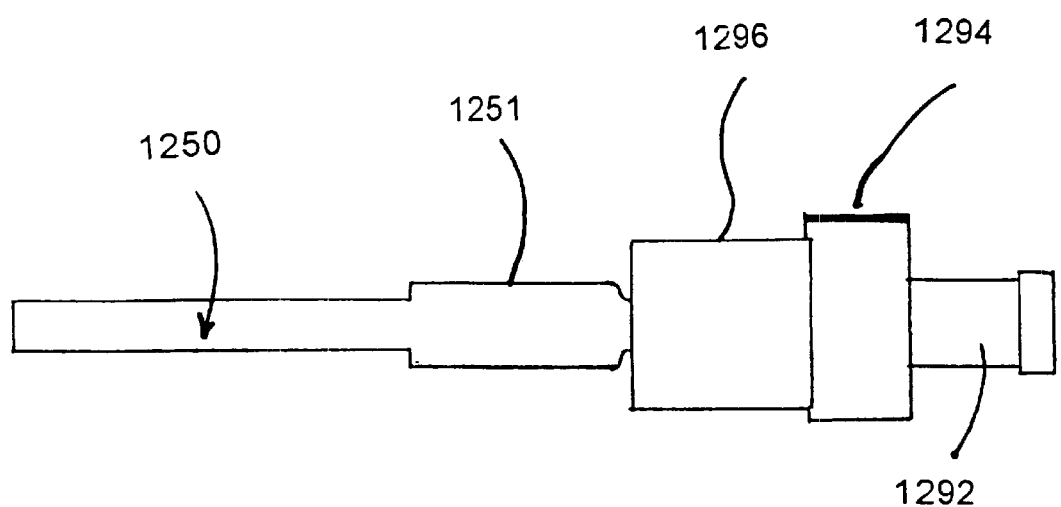
FIG. 12I is a perspective view of control means for inner and outer control rods and a wire deployment rack.
Figure 12J:
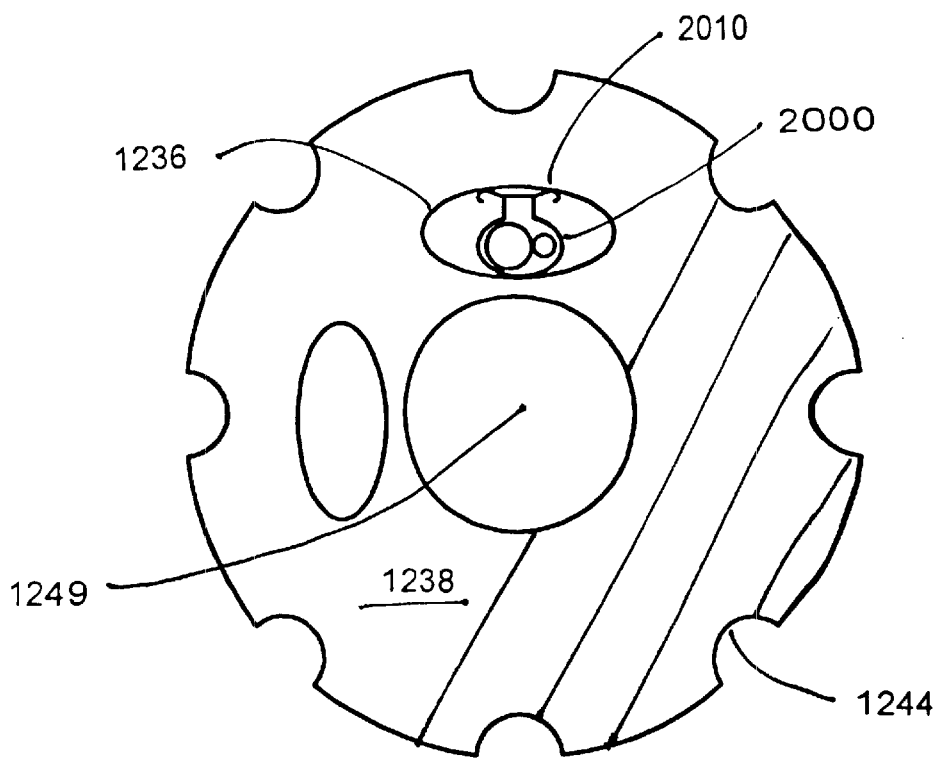
FIG. 12J is a cross-sectional view of a inner control rod illustrating a floating conduit.

As shown in FIGS. 12A and 12I, a handle 1294 is secured to the distal end of the C-shaped backbone member 1240. The handle 1294 enables a surgeon to manipulate or control swing arms 1210, 1220 with respect to inner and outer control rod 1230, 1250 through inner control rod 1230.

A second handle 1296 (illustrated in FIGS. 12A and 12I) for manipulating or controlling wire deployment rack 1270. The second handle 1296 enables a surgeon to manipulate or control the deployment or retraction of the wire cage 1260 through wire deployment rack 1270.

The outer control rod 1250 may be controlled by outer surface portion 1251 extending out of the body cavity (FIGS. 12A and 12I). The surgeon may grip or contact the outer surface to manipulate or control swing arms 1230, 1250.

Figure 12K:
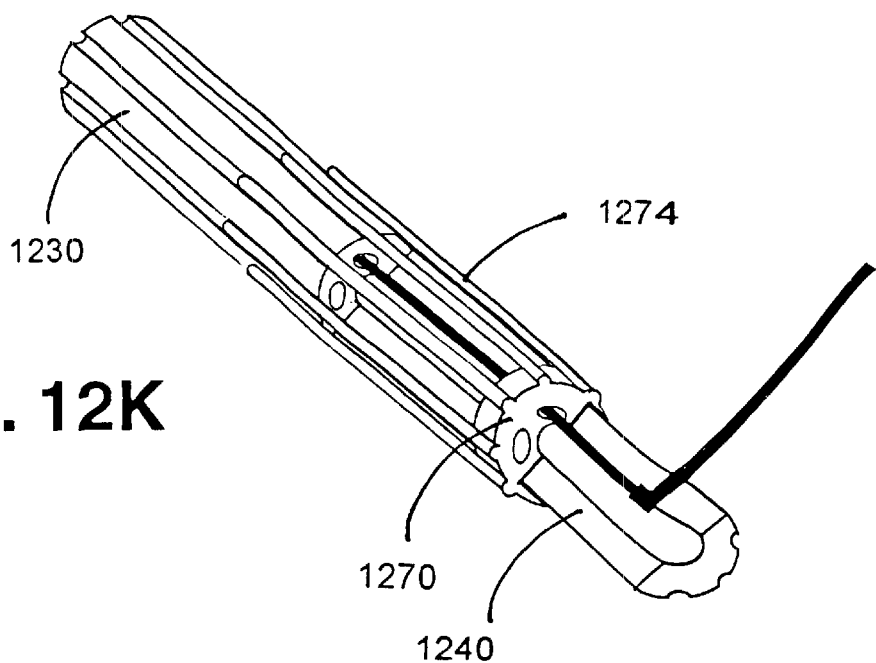
FIG. 12K is a perspective view illustrating access to the floating conduits.

In alternate embodiments, the bores 1236 defined in inner control rod 1230 may include floating conduits 200.0 having a spring 2010 (FIG. J) on top to allow sliding action in the bores 1236. The floating conduits 2000 serve as dividers or isolators for data lines, wires, or the like to isolation bag 20. FIG. 12K illustrates one way in which the surgeon would access the floating conduits 2000.

As assembled, wire extensions 1274 of wire deployment rack 1270 are inserted into grooves 1244 on outer surface 1246 of elongated rod 1238 while engaging surface 1284 of base member 1272 of wire deployment rack 1270 mates with engaging surface 1248 of backbone member 1240 of inner control rod 1230. The wires 1260 are then soldered or compression fitted to distal ends 1276 of wire extensions 1274 of wire deployment rack 1270. Inner control rod 1230 is then slid into outer control rod 1250. The swing arms 1210, 1220 are pivotably attached to inner and outer control rods 1230, 1250. This assembly is then deployed through a delivery trochar so that swing arms 1210, 1220 and wires 1260 may be deployed by handles 1294, 1296, respectively, into isolation bag 20. It is understood that alternate assembly methods may be used.

Tissue mass 10 is manipulated into the cage created by wires 1260. Current is supplied to conductive surfaces 1214, 1224 of swing arms 1210, 1220, respectively, and wire extensions 1274. Handle 1294 is then manipulated to retract wire deployment rack 1270 with wires 1260 so that the tissue mass contacts conductive surfaces 1214, 1224. Tissue mass 10 is then segmented by mechanical and electro-surgical means by the wires 1260 in the same manner as described above. After the tissue mass 10 has been reduced or segmented or reduced into smaller, thinner pieces, the assembly is removed through the delivery trochar and the pieces of tissue mass are removed from body cavity 30 using the methods as described above.

The invention has been described with reference to a number of embodiments with accompanying figures as examples. However, it will be apparent to those of ordinary skill in the art that different aspects or embodiments of the invention may be accomplished independently of each other and that other embodiments and combinations, not expressly described in the specification, will achieve the objections of the invention. As such, embodiments that accomplish the objectives of the invention are equally suitable and are understood to be disclosed by this specification even if not expressly described in the specification.

What is claimed is:

1. A device for reducing tissue mass comprising:
   an isolation bag surrounding the tissue mass, the bag having an inner conductive layer, the inner conductive layer constituting a first electrode;
   a trochar extending into the isolation bag;
   a probe introduced into the bag through the trochar to contact the tissue mass, the probe constituting a second electrode; and
   a source of electrical current for supplying electrical current to the probe and the inner layer of the bag;
   wherein the probe includes a plurality of independent conductive electrodes and each electrode is supplied by an independent source of electrical current.

2. The device of claim 1, wherein each electrode is connected to a multi-channel control unit.

3. The device of claim 2, wherein the control unit is coupled to a A/C generator.

4. A device for reducing tissue mass comprising:
   an isolation bag surrounding the tissue mass, the bag having an inner conductive layer, the inner conductive layer constituting a first electrode;
   a trochar extending into the isolation bag;
   a probe introduced into the bag through the trochar to contact the tissue mass, the probe constituting a second electrode; and
   a source of electrical current for supplying electrical current to the probe and the inner layer of the bag;
   wherein the probe includes a plurality of independent conductive electrodes and the electrodes are formed of segmented disks stacked in a rod-like arrangement.

5. The device of claim 1, wherein the inner conductive layer of the isolation bag comprises a mesh layer.

6. The device of claim 1, wherein the inner conductive layer of the isolation bag comprises an electrical grid.

7. The device of claim 1, wherein the bag includes an outer non-conductive layer.

8. A device for reducing tissue mass comprising:
   an isolation bag surrounding the tissue mass, the bag having an inner conductive layer and an outer non-conductive layer, the inner conductive layer constituting a first electrode;
   a trochar extending into the isolation bag;
   a probe introduced into the bag through the trochar to contact the tissue mass, the probe constituting a second electrode; and
   a source of electrical current for supplying electrical current to the probe and the inner layer of the bag, wherein the outer non-conductive layer comprises sensors to detect current leakage.

9. A device for reducing tissue mass comprising:
   an isolation bag surrounding the tissue mass, the bag having an inner conductive layer and an outer non-conductive layer, the inner conductive layer constituting a first electrode;
   a trochar extending into the isolation bag;
   a probe introduced into the bag through the trochar to contact the tissue mass, the probe constituting a second electrode; and
   a source of electrical current for supplying electrical current to the probe and the inner layer of the bag, wherein the outer non-conductive layer comprises sensors to monitor temperature.

10. The device of claim 1, wherein pressure inside the isolation bag is adjustable.

11. A device for segmenting tissue mass comprising:
    an isolation bag having an open end, the bag being capable of being introduced into a body cavity while in a collapsed state and being expandable from the collapsed state to an expanded state to surround the tissue mass when inserted into the body cavity, the open end of the bag containing the tissue mass positioned outside the body cavity;
    a trochar having a distal cap end and a moveable proximal cap end;
    a cage of electrosurgical wires capable of surrounding the tissue mass, the wires having ends connected to the proximal cap end, the cage of electrosurgical wires held in formation by the distal cap end of the trochar and retracted by moving the proximal cap end;
    a center rod that passes through the trochar and into the bag;
    a source of electrical current for supplying current to the cage of electrosurgical wires and the center rod.

12. The device of claim 11, wherein the center rod comprises a center electrode surrounded by a first insulator and a second insulator.

13. The device of claim 12, wherein the second insulator prevents the cage of electrosurgical wires from contacting the center electrode.

14. The device of claim 12, wherein the center rod is manipulated by the first insulator.

15. A device for reducing tissue mass in a body cavity comprising:
    an insulated bag having an open end, the bag being capable of being introduced into the body cavity while in a collapsed state and being expandable from the collapsed state to an expanded state to surround the tissue mass, the open end of the bag containing the tissue mass being withdrawn from the body cavity;
    a trochar having a distal end;
    a wall comprising a right end cap, a left end cap, and a conductive surface on one side of the wall facing the tissue mass, the wall deployable into the bag through the trochar;
    at least one wire loop positioned within the bag, the loop having ends that pass through the right and left end caps of the wall;

tensioning means for applying tension to at least one of the ends of the loop to reduce the diameter of the loop so that the tissue mass contacts the conductive surface of the wall; and a source of electrical current for supplying current to the conductive surface and the wire loop, wherein an electrical path is formed between the loop and the conductive surface.

16. The device of claim 15, wherein the wall further comprises a non-conductive surface on a second side of the wall, the non-conductive surface extending between the right and left end cap.

17. The device of claim 15, wherein an extension wall is deployable from a center space defined between the conductive and non-conductive surfaces of the wall.

18. The device of claim 17, wherein the extension wall comprises a conductive surface facing the tissue mass.

19. The device of claim 18, wherein current is supplied to the conductive surface of the extension wall.

20. The device of claim 15, wherein the electrosurgical wires are detachably supported by a support sheet.

21. The device of claim 15, wherein ends of the electrosurgical wires are detachably secured to the wall.

22. The device of claim 20, wherein one end of the electrosurgical wires is attached to a first roller.

23. The device of claim 21, wherein the electrosurgical wires are retracted by a control rod controlling the first roller.

24. The device of claim 15, wherein the outer surfaces of the wall include insulating members.

25. The device of claim 20, wherein ends of the support sheet are detachably secured to the wall.

26. The device of claim 25, wherein one end of the support sheet is attached to a second roller.

27. The device of claim 26, wherein the support sheet is retracted by a control rod controlling the second roller.

28. The device of claim 15, wherein the isolation bag is detachably secured to the wall.

29. A method for segmenting a tissue mass in a body cavity comprising steps of:

holding a device of the type including an insulated bag having an open end, the bag being capable of being introduced into the body cavity while in a collapsed state and being expandable from the collapsed state to an expanded state to surround the tissue mass, the open end of the bag containing the tissue mass being withdrawn from the body cavity;

a trochar having a distal end;

a swing arm assembly comprising a plurality of swing arm members, each swing arm member having a conductive surface facing the tissue mass, the swing arms deployable into the bag through the trochar;

at least one wire loop positioned within the bag, the loop having ends that pass through slits defined in the swing arm members;

tensioning means for applying tension to at least one of the ends of the loop to reduce the diameter of the loop so that the tissue mass contacts the conductive surface of the wall;

a source of electrical current for supplying current to the conductive surface and the wire loop, wherein an electrical path is formed between the loop and the conductive surface;

surrounding the tissue mass with an isolation bag, the isolation bag including an open end; and segmenting the tissue mass into a plurality of smaller pieces by creating an electrical path between at least one wire loop and a deployable electrically conducting surface by applying tension to the wire loops.

30. The method of claim 29, further comprising the step of withdrawing the open end of the isolation bag outside the body cavity.

31. A method for reducing a tissue mass in a body cavity comprising steps of:

holding a device of the type including an insulated bag having an open end, the bag being capable of being introduced into the body cavity while in a collapsed state and being expandable from the collapsed state to an expanded state to surround the tissue mass, the open end of the bag containing the tissue mass being withdrawn from the body cavity;

a trochar having a distal end;

a swing arm assembly comprising a plurality of swing arm members, each swing arm member having a conductive surface facing the tissue mass, the swing arms deployable into the bag through the trochar;

at least one wire loop positioned within the bag, the loop having ends that pass through slits defined in the swing arm members;

tensioning means for applying tension to at least one of the ends of the loop to reduce the diameter of the loop so that the tissue mass contacts the conductive surface of the wall;

a source of electrical current for supplying current to the conductive surface and the wire loop, wherein an electrical path is formed between the loop and the conductive surface;

surrounding the tissue mass with an isolation bag, the isolation bag including an open end; and segmenting the tissue mass into a plurality of smaller pieces by creating an electrical path between an electrically conducting inner layer of the isolation bag and a probe having at least one electrically exposed electrode.

32. The method of claim 31, further comprising the step of withdrawing the open end of the isolation bag outside the body cavity.

33. A device for reducing tissue mass in a body cavity comprising:

an insulated bag having an open end, the bag being capable of being introduced into the body cavity while in a collapsed state and being expandable from the collapsed state to an expanded state to surround the tissue mass, the open end of the bag containing the tissue mass being withdrawn from the body cavity;

a trochar having a distal end;

a swing arm assembly comprising a plurality of swing arm members, each swing arm member having a conductive surface facing the tissue mass, the swing arms deployable into the bag through the trochar;

at least one wire loop positioned within the bag, the loop having ends that pass through slits defined in the swing arm members;

tensioning means for applying tension to at least one of the ends of the loop to reduce the diameter of the loop so that the tissue mass contacts the conductive surface of the wall; and a source of electrical current for supplying current to the conductive surface and the wire loop, wherein an electrical path is formed between the loop and the conductive surface.

34. The device of claim 33, wherein the swing arms are nested while in an undeployed position.

35. The device of claim 33, wherein the swing arms are pivotably secured to an inner control rod and an outer control rod, the inner control rod is slidably received by the outer control rod, the inner and outer control rods are slidably received by the trochar.

36. The device of claim 35, wherein the inner control rod comprises a rod and a backbone member protruding from an end of the rod, wherein the elongated rod has an outer surface defining a plurality of grooves for receiving the wires.

37. The device of claim 36, wherein the outer control rod comprises a tube having an inner surface defining a plurality of grooves for receiving the wires that align with the grooves defined in the outer surface of the elongated rod when the outer control rod receives the inner control rod.

38. The device of claim 37, wherein ends the wires are attached to a wire deployment rack to shorten the length of the wires.

39. The device of claim 36, wherein the wire deployment rack comprises a plurality of wire extensions extending from a base member to attached with the ends of the wires.

40. The device of claim 39, wherein the base member includes an engaging surface that mates with an engaging surface of the backbone member.

41. The device of claim 40, wherein the wire deployment rack attaches to a handle for manipulating the wire cage.

42. The device of claim 41, wherein the inner control rod attaches to a second handle for manipulating the swing arms with respect to the inner control rod and outer control rod.

43. The device of claim 35, wherein inner control rod defines at least one bore serving as a conduit for electrical wires from the current source to the conductive surfaces of the swing arms.

44. The device of claim 35, wherein a plurality of wire loops form a wire cage.

45. The device of claim 44, wherein the plurality of wire loops are held together at their apexes by a control point button.

46. The device of claim 45, wherein the control point button is controllable by a button control rod passing through a center bore defined in the inner control rod, the button control rod controllable by a surgeon outside the body cavity.

* * * * *